(12) United States Patent
Mellis et al.

(10) Patent No.: US 7,459,426 B2
(45) Date of Patent: Dec. 2, 2008

(54) METHODS OF USING IL-1 ANTAGONISTS TO TREAT AUTOINFLAMMATORY DISEASE

(75) Inventors: Scott Mellis, New Rochelle, NY (US); Margaret Karow, Putnam Valley, NY (US); George D. Yancopoulos, Yorktown Heights, NY (US); Joanne Papadopoulos, LaGrangeville, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 241 days.

(21) Appl. No.: 11/144,987

(22) Filed: Jun. 3, 2005

(65) Prior Publication Data

US 2005/0272655 A1 Dec. 8, 2005

Related U.S. Application Data

(60) Provisional application No. 60/577,023, filed on Jun. 4, 2004.

(51) Int. Cl.
*A61K 38/00* (2006.01)
*A61K 38/19* (2006.01)
*C12N 15/00* (2006.01)

(52) U.S. Cl. .................. 514/2; 424/85.1; 435/69.1
(58) Field of Classification Search ................ None
See application file for complete search history.

(56) References Cited

U.S. PATENT DOCUMENTS

| 6,927,044 B2* | 8/2005 | Stahl et al. ............... 435/69.7 |
| 2001/0053764 A1* | 12/2001 | Sims et al. ............... 514/12 |
| 2003/0143697 A1 | 7/2003 | Stahl et al. |
| 2005/0129685 A1* | 6/2005 | Cao et al. ................ 424/143.1 |

FOREIGN PATENT DOCUMENTS

WO    WO 2004/022718    3/2004

OTHER PUBLICATIONS

Galeazzi et al., Clin. Exp. Rheumatol., 2006, 24(1 Suppl. 40):S79-85 (abstract).*
Rotondi et al., Endocri. Rev., 2007, 28(5): 492-520.*
Aksentijevich, I., et al. (2002) Arthritis & Rheumatism, vol. 46, No. 12, pp. 3340-3348.
Pascual, V., et al. (2005) JEM The Rockefeller University Press, vol. 201, No. 9, pp. 1479-1486.
Stehlik, C., et al. (2004) J. Exp. Med. The Rockefeller University Press, vol. 200, No. 5, pp. 551-558.
Dinarello, C.A., (2005) JEM The Rockefeller University Press, vol. 201, No. 9, pp. 1355-1359.
Hawkins, P.N., et al. (2004) Arthritis & Rheumatism, vol. 50, No. 2, pp. 607-612.
Hoffman, H.M., et al. (2004) Arthritis & Rheumatism, vol. 50, No. 2, pp. 345-349.
Amgen, Inc.—Kineret™ (anakinra) Prescribing Instructions, Dec. 15, 2006.
Canna, S. et al. (2005) Treatment of 4 Patients wiht Cryoporin-Associated Periodic . . . Arthritis & Rheumatism 52(9, Suppl) : Abstract 672.
Carter, John D. et al. (2003) Letters to the Editor: Crohn Disease Worsened by Anakinra Administration, J. Clin. Rheumatology 9(4) : 276-277.
Hawkins, P.N. et al. (2003) Letter: Interleukin-1 Receptor Antagonist in Muckle-Wells Syndrome, N. Eng. J. Med. 348:2583-2584.
Lovell, D. J. (2007) Preliminary Evidence for . . . Bioactivity of IL-1 Trap . . . in SJIA, Arthritis & Rheumatism, 56(9, Suppl) :S514, Abstract 1282.
Shroff, S. et al. (2007) Safety and Efficacy of IL-1 Trap in Patients with Familial . . . Arthritis & Rheumatism, 56(9, Suppl) :S365, Abstract 874.

* cited by examiner

*Primary Examiner*—Elizabeth C Kemmerer
*Assistant Examiner*—Xiaozhen Xie
(74) *Attorney, Agent, or Firm*—Tor Smeland, Esq.; Valeta Gregg, Esq.

(57) ABSTRACT

Methods of treating, inhibiting, or ameliorating an autoinflammatory disorder, disease, or condition in a subject in need thereof, comprising administering to a subject in need a therapeutic amount of an interleukin 1 (IL-1) antagonist, wherein the autoinflammatory disorder, disease, or condition is treated, inhibited, or ameliorated. The IL-1 antagonist is a molecule capable of binding and inhibiting IL-1. The therapeutic methods are useful for treating a human adult or child suffering from Neonatal Onset Multisystem Inflammatory Disorder (NOMID/CINCA), Muckle-Wells Syndrome (MWS), Familial Cold Autoinflammatory Syndrome (FCAS), familial mediterranean fever (FMF), tumor necrosis factor receptor-associated periodic fever syndrome (TRAPS), or systemic onset juvenile idiopathic arthritis (Still's Disease).

6 Claims, No Drawings

ID NO: 4, 6, 8, 10, 12, 14, 16, 18, 20, 22, 24, 26. A preferred

METHODS OF USING IL-1 ANTAGONISTS TO TREAT AUTOINFLAMMATORY DISEASE

RELATED APPLICATIONS

This application claims the benefit under 35 USC 119(e) to U.S. Ser. No. 60/577,023 filed 4 Jun. 2004, which application is incorporated by reference in its entirety.

BACKGROUND

1. Field of the Invention

The invention relates to methods of using interleukin-1 (IL-1) antagonists to treat autoinflammatory diseases, such as, for example, including familial mediterranean fever (FMF), NOMID/CINCA, Muckle-Wells Syndrome, FCAS, and tumour necrosis factor receptor-associated periodic fever syndrome (TRAPS).

2. Description of Related Art

One important group of autoinflammatory disorders encompasses autosomal dominant conditions associated with mutations in CIAS-1, a gene that encodes a pyrin-related protein called "cryopyrin" (Feldmann et al. (2002) Am. J. Hum. Genet. 71:198-203; Hoffman et al. (2001) Nat. Genet. 29:301-305). These disorders include Neonatal Onset Multisystem Inflammatory Disorder (NOMID/CINCA), Muckle-Wells Syndrome (MWS), and Familial Cold Autoinflammatory Syndrome (FCAS). These disorders present a spectrum of clinical manifestations ranging from FCAS being the mildest to the seriously disabling disease of NOMID/CINCA. An urticaria-like skin rash is common to the entire spectrum of these diseases. In patients with FCAS, this rash is inducible by cold exposure while most patients with MWS or NOMID present with daily rashes that are consistently provoked by a number of different stimuli. Conjunctivitis is present in all forms of disease expression, however, hearing loss, aseptic meningitis and arthritis are mainly seen in patients with MWS and NOMID/CINCA. The disfiguring and disabling body overgrowth at the epiphyses and patellae is only seen in patients with NOMID/CINCA.

FMF is a recessively inherited condition characterized by episodes of fever and serositis or synovitis; some subjects also develop systemic amyloidosis (Balow et al. (1997) Genomics 44:280-291). The FMF gene encodes a novel protein called pyrin that is the prototype of a family of molecules involved in the regulation of apoptosis (cell-death) and inflammation. The precise biochemical mechanism by which these proteins function, and by which mutations cause disease, is still unknown.

Still's Disease (systemic onset juvenile idiopathic arthritis), is manifest by spiking fevers, evanescent salmon color rash, arthritis, arthralgia, and hepatosplenomegaly (Masson et al. (1995) Rev. Rhum. Engl. Ed. 62:748-757; Spiegel et al. (2000) Arthritis Rheum. 43:2402-2409). There are as yet no definitive genetic associations with Still's Disease and the pathogenesis is poorly understood. Interestingly, many of the signs and symptoms of Still's disease are similar to those with autoinflammatory disease. Still's Disease typically first occurs during childhood, but can also have its onset in adulthood.

Similarly, Kawasaki disease is a disease affecting children that is accompanied by fevers, swelling and arthritic joints, and rash, as well as vascular inflammation that can cause permanent coronary damage in approximately 15-25% of affected children. Two other similar diseases are Blau's syndrome and Early Onset Sarcoidosis (EOS), both of which are caused by a gain of function mutations in NOD2, a protein similar to Pyrin, and cause rash, granulomatosis, arthritis and uveitis. Other diseases that have also been considered autoinflammatory include, Hidradenitis suppurativa, Behcet's, hyperimmunoglobulinemia D with periodic fever syndrome (HIDS), tumour necrosis factor receptor-associated periodic fever syndrome (TRAPS), and Pyogenic sterile arthritis, pyoderma gangrenosum and acne (PAPA syndrome).

The pathogenesis of autoinflammatory disease is not completely understood. There is a growing body of evidence that interleukin-1 (IL-1) plays a role in a number of these conditions and that targeting of this cytokine can provide important benefits (Hoffman et al. (2004) Arthritis. Rheum. 50:345-349). There is clearly a need to develop improved therapeutic treatment of these autoinflammatory diseases.

BRIEF SUMMARY OF THE INVENTION

In a first aspect, the invention features a method of treating, inhibiting, or ameliorating an autoinflammatory disorder, comprising administering to a subject in need an interleukin 1 (IL-1) antagonist. An IL-1 antagonist is a compound capable of blocking or inhibiting the biological action of IL-1, including IL-1-binding fusion proteins. In a preferred embodiment, the IL-1 antagonist is an IL-1-specific fusion protein comprising two IL-1 receptor components and a multimerizing component, for example, an IL-1 fusion protein trap antagonist (an "IL-1 trap") described in U.S. patent publication No. 2003/0143697, published 31 Jul. 2003, herein specifically incorporated by reference in its entirety. In a specific embodiment, the IL-1 antagonist is the fusion protein shown in SEQ ID NO: 4, 6, 8, 10, 12, 14, 16, 18, 20, 22, 24, 26. A preferred fusion protein is shown in SEQ ID NO:10. The invention encompasses the use of an IL-1-binding fusion protein substantially identical to the protein of SEQ ID NO: 4, 6, 8, 10, 12, 14, 16, 18, 20, 22, 24, 26, that is, a protein having at least 95% identity, at least 97% identity, at least 98% identity to the protein of SEQ ID NO: 4, 6, 8, 10,12, 14, 16, 18, 20, 22, 24, 26 and capable of binding and inhibiting IL-1. Further, in specific embodiments, the IL-1 antagonist is a fusion protein comprising one or more immunoglobulin-derived components in place of one or more receptor components. In specific embodiments, the IL-1 antagonist comprises one or more immunoglobulin-derived components specific for IL-1 and/ or an IL-1 receptor.

The subject being treated is most preferably a human diagnosed as suffering from an autoinflammatory disorder. More specifically, the subject is a human adult or child diagnosed with an autoinflammatory disorder associated with mutations in CIAS-1, such as Neonatal Onset Multisystem Inflammatory Disorder (NOMID/CINCA), Muckle-Wells Syndrome (MWS), Familial Cold Autoinflammatory Syndrome (FCAS); familial Mediterranean fever (FMF); systemic onset juvenile idiopathic arthritis (Still's Disease), tumour necrosis factor receptor-associated periodic fever syndrome (TRAPS), or Kawasaki Disease.

The method of the invention includes administration of the IL-1 antagonist by any means known to the art, for example, subcutaneous, intramuscular, intranasal, intravenous, transdermal administration or oral routes of administration. Preferably, administration is subcutaneous or intravenous.

In a second aspect, the invention features a method of treating, inhibiting, or ameliorating a disease or condition selected from the group consisting of NOMID/CINCA, MWS, FCAS, FMP, Still's Disease, TRAPS, and Kawasaki Disease, the method comprising administering to a subject in need an interleukin 1 (IL-1) antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 antagonist is shown in SEQ ID NO:10. Preferably, the subject treated is a child or adult human diagnosed with the disease or condition.

In a third aspect, the invention features a method of treating, inhibiting, or ameliorating Neonatal Onset Multisystem Inflammatory Disorder (NOMID/CINCA), comprising administering to a subject in need an interleukin 1 (IL-1) antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 antagonist is shown in SEQ ID NO:10.

In a fourth aspect, the invention features a method of treating, inhibiting, or ameliorating Muckle-Wells Syndrome (MWS), the method comprising administering to a subject in need an interleukin 1 (IL-1) antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 antagonist is shown in SEQ ID NO:10.

In a fifth aspect, the invention features a method of treating, inhibiting, or ameliorating Familial Cold Autoinflammatory Syndrome (FCAS) the method comprising administering to a subject in need an interleukin 1 (IL-1) antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 antagonist is shown in SEQ ID NO:10.

In a sixth aspect, the invention features a method of treating, inhibiting, or ameliorating familial mediterranean fever (FMF), the method comprising administering to a subject in need an interleukin 1 (IL-1) antagonist. In a preferred embodiment, the IL-1 antagonist is a fusion protein capable of trapping IL-1. In a specific embodiment, the IL-1 trap is the fusion protein shown in SEQ ID NO:4, 6, 8, 10,12, 14, 16, 18, 20, 22, 24, 26, or a substantially identical protein capable of binding and inhibiting IL-1. A preferred IL-1 trap is shown in SEQ ID NO:10.

In a seventh aspect, the invention features a method of treating, inhibiting, or ameliorating systemic onset juvenile idiopathic arthritis (Still's Disease), the method comprising administering to a subject in need an interleukin 1 (IL-1) antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 trap is shown in SEQ ID NO:10.

In an eighth aspect, the invention features a method of treating, inhibiting, or ameliorating tumour necrosis factor receptor-associated periodic fever syndrome (TRAPS), the method comprising administering to a subject in need an IL-1 antagonist. In a preferred embodiment, the IL-1 antagonist is a fusion protein capable of trapping IL-1. In a specific embodiment, the IL-1 antagonist is the fusion protein shown in SEQ ID NO: 4, 6, 8, 10, 12, 14, 16, 18, 20, 22, 24, 26, or a substantially identical protein capable of binding and inhibiting IL-1. A preferred IL-1 trap is shown in SEQ ID NO:10.

In specific embodiments of the therapeutic method of the invention, the subject is treated with a combination of a first IL-1-binding fusion protein trap molecule and a second therapeutic agent. The second therapeutic agent may be a second IL-1 antagonist, such as, for example, a second IL-1-binding fusion protein trap, anakinra (Kineret®, Amgen), a recombinant, nonglycosylated form of the human IL-1 receptor antagonist (IL1Ra), or an anti-IL-18 drug such as IL-18BP or a derivative, an IL-18-binding fusion protein trap (an "IL-18 trap"), anti-IL-18, anti-IL-18RI, or anti-IL-18Racp antibodies or antibody fragments. Other co-therapies include low dose colchine for FMF, aspirin or other NSAIDs, steroids such as prednisolone, methotrexate, low dose cyclosporine A, TNF inhibitors such as Enbrel®, or Humira®, other inflammatory inhibitors such as inhibitors of caspase-1, p38, IKK1/2, CTLA-4Ig, anti-IL-6 or anti-IL6Ra, etc.

In a ninth aspect, the invention features a therapeutic method of treating an autoinflammatory disease or condition, comprising administering a pharmaceutical composition comprising an IL-1-binding fusion protein trap and a pharmaceutically acceptable carrier. In one embodiment, the IL-1-binding fusion protein trap is administered in a dose range of 1-20 mg/kg on a weekly basis for a treatment period of between 1 week to one year or more. In another embodiment, a total IL-1-binding fusion protein is administered in the range of 50-2000 mg, which may be provided in a single dose or in sequential doses over a period of time such as a period of weeks or months.

Other objects and advantages will become apparent from a review of the ensuing detailed description.

DETAILED DESCRIPTION

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only to the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference in their entirety.

General Description

Mutations in the gene CIAS1 are now recognized as being responsible for three rare genetic syndromes: Neonatal Onset Multisystem Inflammatory Disorder (NOMID), Muckle-Wells Syndrome (MWS), and Familial Cold Autoinflammatory Syndrome (FCAS). (Hoffman et al. 2001 Naure 29:301-305; Feldmann et al. 2002 Am J Hum Genet 71:198-203; Aksentijevich et al. 2002 Arthritis Rheum 46:3340-3348). In aggregate, these conditions are known as "CAPS", an acronym for "CIAS1 Associated Periodic Syndromes". CAPS disorders are exceedingly rare; with approximately 200-300 adults and children in the U.S. with FCAS and significantly fewer adults with NOMID or MWS known to have these conditions. The rarity of these conditions, particularly NOMID and MWS, are probably due to effects of disease severity on survival or reproductive fitness.

CAPS are inherited in an autosomal dominant manner, with a sporadic or familial pattern. CIAS1 encodes a protein called NALP3 that is a component of the "inflammasome", a subcellular enzyme complex that regulates the activity of caspase 1. Caspase 1 is the enzyme that cleaves the inactive pro-form of the proinflammatory cytokine, IL-1, into its biologically active form (Agostini et al. 2004 supra). Mutations in CIAS1 lead to increased production of IL-1 and numerous pathological consequences (Aksentijevich et al. 2002 supra). IL-1 strongly induces the production of acute phase reactants in the liver, such as C-reactive protein (CRP) and serum amyloid A (SAA).

The genetics of CAPS are interesting in that there can be a number of different point mutations in CIAS1 associated with these syndromes (Sarrauste de Menthiere et al. 2003 Nucleic Acids Res 31:282-285; Aksentijevich et al. 2002 supra). Some of these mutations are associated with only one syndrome; others two. For example, some mutations may be associated with FCAS as well as MWS; other mutations may be associated with MWS and NOMID. Approximately 50% of patients with NOMID do not have a recognized mutation in the coding region of CIAS1. In these patients, the disease may be due to an as-yet-unrecognized mutation in a regulatory region or protein of CIAS1, or in another gene encoding a closely-related protein in this pathway. FCAS is more genetically homogeneous than NOMID; almost all patients with FCAS share a common mutation (Sarrauste de Menthiere et al. 2003 supra; Hoffman et al. 2001 supra).

CAPS disorders share common clinical features and present as a spectrum of clinical severity. NOMID is the most seriously disabling, MWS somewhat less so and FCAS is the least severe. CAPS disorders have overlapping features and there are individuals and kindred with unique constellations of signs and symptoms. Features common to all these conditions include fevers, urticaria-like rash, arthritis or arthralgia, myalgia, malaise, and conjunctivitis. However, the spectrum of symptoms for any patient with a CAPS disorder may differ from that of another patient with the same disorder. A universal feature of active CAPS disease is laboratory test elevation of acute phase reactants, such as CRP, SAA, and/or erythrocyte sedimentation rate (ESR).

In NOMID, chronic aseptic meningitis may lead to mental retardation and these patients may also suffer disfiguring and disabling bony overgrowth at the epiphyses and patellae. These patients may also suffer blindness due to optic nerve atrophy that results from increased intracranial pressure. MWS and NOMID are commonly associated with severe inflammation that may include the auditory system, meninges, and joints. These patients may suffer daily high spiking fevers and a chronic rash that frequently changes in distribution and intensity. Patients may suffer hearing loss or deafness. Conjunctivitis and papilledema are frequently observed. Amyloidosis may develop and lead to renal failure due to chronic inflammation and overproduction of acute phase reactants (particularly SM). MWS is also known as "amyloidosis-deafness syndrome".

The clinical signs and symptoms of FCAS are induced by exposure to modestly cold air (e.g., seasonal temperature changes, air conditioning). Patients may have frequent (sometimes daily) episodes of a painful or pruritic rash, fever, fatigue, malaise, headache, nausea, and thirst during cold months or in locations where air conditioning is prevalent. In many locales, this may include most work places. FCAS is a source of frequent pain to patients and may restrict their employment, social, and recreational opportunities. Up to 2% of patients with FCAS develop amyloidosis, a life-threatening condition. This frequency is substantially higher than the rate of amyloidosis in the general community. The genetics and natural history of FCAS are described in detail Hoffman et al. 2001 Nature 29:301-305 and Hoffman et al. 2001 J Allergy din Immunol 108:615-620, which publications are herein specifically incorporated by reference in their entirety.

Definitions

By the term "blocker", "inhibitor", or "antagonist" is meant a substance that retards or prevents a chemical or physiological reaction or response. Common blockers or inhibitors include but are not limited to antisense molecules, antibodies, antagonists and their derivatives. More specifically, an example of an IL-1 blocker or inhibitor is an IL-1 antagonist including, but not limited to, an IL-1 fusion protein trap antagonist, which binds and inhibits IL-1.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

By the term "substantially identical" is meant a protein sequence having at least 95% identity to an amino acid sequence selected from the group consisting of the amino acid sequences SEQ ID NOs: 4, 6, 8, 10, 12, 14, 16, 18, 20, 22, 24, and 26, and capable of binding IL-1 and inhibiting the biological activity of IL-1.

The term "identity" or "homology" is construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions will be construed as reducing identity or homology. Methods and computer programs for the alignment are well known in the art. Sequence identity may be measured using sequence analysis software (e.g., Sequence Analysis Software Package, Genetics Computer Group, University of Wisconsin Biotechnology Center, 1710 University Ave., Madison, Wis. 53705). This software matches similar sequences by assigning degrees of homology to various substitutions, deletions, and other modifications.

IL-1-Binding Fusion Protein Trap Antagonists

Interleukin-1 (IL-1) traps are multimers of fusion proteins containing IL-1 receptor components and a multimerizing component capable of interacting with the multimerizing component present in another fusion protein to form a higher order structure, such as a dimer. The IL-1-binding fusion proteins useful in the methods of the invention include two distinct receptor components that bind a single cytokine, resulting in the generation of antagonists with dramatically increased affinity over that offered by single component reagents. The IL-1-binding fusion protein traps are comprised of the extracellular domain of human IL-1R Type I (IL-1RI) or Type II (IL-1RII) followed by the extracellular domain of human IL-1 Accessory protein (IL-1AcP), followed by a multimerizing component. In a preferred embodiment, the multimerizing component is an immunoglobulin-derived domain, such as, for example, the Fc region of human IgG, including part of the hinge region, the CH2 and CH3 domains. An immunoglobulin-derived domain may be selected from any of the major classes of immunoglobulins, including IgA, IgD, IgE, IgG and IgM, and any subclass or isotype, e.g. IgG1, IgG2, IgG3 and IgG4; IgA-1 and IgA-2. Alternatively, the IL-1-binding fusion proteins useful in the method of the invention are comprised of the extracellular domain of human IL-1AcP, followed by the extracellular domain of human IL-1RI or IL-1RII, followed by a multimerizing component. For a more detailed description of the IL-1-binding fusion protein traps, see WO 00/18932, which publication is herein specifically incorporated by reference in its entirety. Preferred IL-1 antagonists have the amino acid sequence shown in SEQ ID NOs: 2, 4, 6, 8, 10, 12, 14, 16, 18, 20, 22, 24, and 26, or a substantially identical protein at least 95% identity to a sequence of SEQ ID NO: 4, 6, 8, 10, 12, 14, 16, 18, 20, 22, 24, or 26, and capable of binding and inhibiting IL1.

Treatment Population

The therapeutic methods of the invention are useful for treating individuals affected with CIAS-1 mutation disorders (NOMID, MWS, FCAS), FMF, TRAPS, or Still's Disease. Commonly accepted diagnostic criteria for CIAS-1 mutation associated disease (NOMID, MWS, FCAS), Familial Mediterranean Fever, or Still's Disease (adult- or juvenile-onset) are know to those skilled in the art. In the case of patients diagnosed with FMF, the therapeutic method of the invention may be particularly useful for those with disease refractory to therapy with colchicine.

Methods of Administration

The invention provides methods of treatment comprising administering to a subject an effective amount of an agent of the invention. In a preferred aspect, the agent is substantially purified (e.g., substantially free from substances that limit its effect or produce undesired side-effects).

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, intraperitoneal, intravenous, subcutaneous, intranasal, epidural, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, said implant being of a porous, non-porous, or gelatinous material, including membranes, such as sialastic membranes, fibers, commercial skin substitutes or angioplasty balloons or stents.

In another embodiment, the active agent can be delivered in a vesicle, in particular a liposome (see Langer (1990) Science 249:1527-1533). In yet another embodiment, the active agent can be delivered in a controlled release system. In one embodiment, a pump may be used (see Langer (1990) supra). In another embodiment, polymeric materials can be used (see Howard et al. (1989) J. Neurosurg. 71:105). In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

Combination Therapies

In numerous embodiments, the IL-1 antagonists useful in the methods of the present invention may be administered in combination with one or more additional compounds or therapies. Combination therapy may be simultaneous or sequential. The IL-1-binding fusion proteins of the invention may be combined with, for example, TNF-inhibiting agents such as etanercept (Enbrel®, Amgen), infliximab (Remicade®, Centocor), Humira® (Abbott), thalidomide, steroids, anakinra (Kinaret®, Amgen), or colchicine. Colchicine is a mainstay of therapy for subjects with FMF; in this study, subjects will not be removed from treatment with this medication. For Still's Disease (and classical autoinflammatory diseases), compounds such as methotrexate, cyclosporine, chlorambucil, cyclophosphamide (DMARDs) have been used as monotherapy or in combination with no consistent response. Some subjects respond to high doses of steroids. DMARDs, and more recently anti-TNF agents have been used with variable success. The IL-1-binding fusion proteins of the invention may also be combined with anti-IL-18 drugs, such as for example, IL-18BP or a derivative, an IL-18-binding fusion protein, anti-IL-18, anti-IL-18RI, or anti-IL-18Racp. Other co-therapies include low dose colchine for FMF, aspirin or other NSAIDs, steroids such as prednisolone, methotrexate, low dose cyclosporine A, TNF inhibitors such as Enbrel®, or Humira®, other inflammatory inhibitors such as inhibitors of caspase-1, p38, IKK1/2, CTLA4Ig, anti-IL-6 or anti-IL6Ra, etc.

Pharmaceutical Compositions

The present invention also provides pharmaceutical compositions. Such compositions comprise a therapeutically effective amount of an active agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin.

In a preferred embodiment, the composition is formulated in accordance with routine procedures as a pharmaceutical composition adapted for intravenous administration to human beings. Where necessary, the composition may also include a solubilizing agent and a local anesthetic such as lidocaine to ease pain at the site of the injection. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the active agent of the invention which will be effective in the treatment of delayed-type hypersensitivity can be determined by standard clinical techniques based on the present description. In addition, in vitro assays may optionally be employed to help identify optimal dosage ranges. The precise dose to be employed in the formulation will also depend on the route of administration, and the seriousness of the condition, and should be decided according to the judgment of the practitioner and each subject's circumstances. However, suitable dosage ranges for intravenous administration are generally up to about 2 grams of active compound. Effective doses may be extrapolated from dose-response curves derived from in vitro or animal model test systems.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans. Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the compounds that are sufficient to maintain therapeutic effect. In cases of local administration or selective uptake, the effective local concentration of the compounds may not be related to plasma concentration. One having skill in the art will be able to optimize therapeutically effective local dosages without undue experimentation.

The amount of compound administered will, of course, be dependent on the subject being treated, on the subject's weight, the severity of the affliction, the manner of administration, the frequency of administration and the judgment of the prescribing physician. The therapy may be repeated intermittently while symptoms are detectable or even when they are not detectable. The therapy may be provided alone or in combination with other drugs.

Kits

The invention also provides an article of manufacturing comprising packaging material and a pharmaceutical agent contained within the packaging material, wherein the pharmaceutical agent comprises at least one IL-1-specific fusion protein of the invention and wherein the packaging material comprises a label or package insert which indicates that the IL-1-specific fusion protein can be used for treating an autoinflammatory disease or condition.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of IL-1 Trap on Human Autoinflammatory Disease

An initial study is conducted with 15 adult subjects suffering from diseases known to respond to IL-1 blockade (NO-MID/MWS/FCAS) as well as subjects with Adult Still's disease and colchicine-resistant FMF. Subjects are screened for eligibility, clinical symptoms determined, active disease confirmed and baseline blood is drawn on approximately 3 occasions one week apart to determine baseline levels of inflammation. A careful, complete standardized history and physical exam is performed, appropriate for the disease under study to assure uniform data collection on every subject. Vital signs and weight is obtained at each visit. The clinical data is based on a detailed questionnaire including all the reported clinical manifestations. The following evaluation procedures pertain specifically to CIAS-1 mutation associated disorders and are performed as clinically indicated: dermatological evaluation; ophthalmologic evaluation; ear/nose/throat evaluation; neurology evaluation; lumbar puncture; head MRI; radiographs, joint MRI; and pharmacokinetic profiling.

All study subjects receive IL-1-binding fusion protein (SEQ ID NO:10) with a dosing regimen of 100 mg once a day for 3 consecutive days, a regimen expected to provide 2-4 weeks of significant IL-1 inhibitory activity. The primary outcomes are measured during this period and include drug safety, clinical efficacy analysis, and the change in selected biomarkers of inflammation (e.g., acute phase reactants such as CRP, serum amyloid A, and ESR) at Day 10 following initiation of treatment with IL-1 trap. If a favorable response is observed at Day 10, subjects are monitored at predefined timepoints (with no further treatment) until return of signs and symptoms (flare). Upon flare, subjects are eligible for entry into an extension phase that entails re-treatment with the loading regimen (100 mg/day IL-1 trap for three consecutive days) followed by once-weekly dosing with 100 mg IL-1 trap for up to one year.

Based on the Investigator's clinical judgment, an IL-1 trap dose escalation regimen may be implemented if, after 4 weeks of dosing in the extension phase at 100 mg/week, a subject's Month 1 acute phase reactant levels have not normalized (CRP>0.5 mg/dL and/or SAA>10 mg/L) or escalation is warranted based on persistent signs and/or symptoms of disease. The first dose escalation level may be 160 s.c. once weekly. Subjects will be observed for 4 weeks; if criteria for dose escalation are still met, then the dose may be raised to 320 mg s.c. once-weekly.

Preliminary Results. Four subjects with CAPS were initially enrolled. Results indicated that all subjects experienced rapid and extensive improvement in inflammatory signs and symptoms upon treatment with IL-1 trap (SEQ ID NO:10), including improvement in both patient- and physician-reported disease manifestation. Major declines in inflammatory biomarkers, such as CRP and SAA were also observed. Signs and symptoms returned within a median of 21 days (range 9-26) of initial dosing and then responded promptly to re-treatment. Table 1 provides a summary of the daily diary scores, acute phase reactants and clinical assessments (‡Performed on 3 patients; * statistically significant difference from previous time point at p<0.1 level; ** statistically significant difference from previous time point at p<0.05 level). The Physician and Patient global assessment VAS scores mirrored the changes in the acute phase reactants (SM, CRP and ESR) at baseline, at the time of flare, and at a time point designated as reflecting maximal efficacy.

TABLE 1

|  | Baseline median (range) | Maximal Efficacy median (range) | Flare median (range) |
|---|---|---|---|
| Daily Diary Score | 6.06 (2.2-7.56) | 1.67 (0-3.3)* | 4.5 (2-7.33) |
| Acute phase reactants |  |  |  |
| SAA (mg/L) | 96 (16.1-468) | 8.25 (2-19) | 84 (50-236)‡ |
| CRP (mg/dL) | 7.28 (2.32-8.65) | 0.72 (0.07-1.15)** | 2.93 (0.076-6.21) |
| ESR (mm/hr) | 56.67 (22-92) | 24 (7-45)** | 34 (11-70)* |
| Blood Count |  |  |  |
| WBC | 15.28 (9.33-19.4) | 7.58 (7.21-9.9)** | 8.48 (6.34-11.47) |
| Hgb | 12.95 (8.1-14.7) | 13.3 (8.2-15.6)* | 13.1 (7.9-14.57) |
| Plt | 356.5 (291-445.5) | 303.25 (240-377)** | 291 (257-359.3) |
| Questionnaires‡ |  |  |  |
| Physician global VAS (cm) | 6.85 (4.1-6.95) | 0.2 (0.2-2.6) | 3.3 (3.1-3.5) |
| Patient global VAS (cm) | 5.2 (3.95-6.9) | 1.1 (0.95-3.05)** | 3.6 (3.1-6.45)** |
| Fatigue VAS (cm) | 5.55 (3.25-8) | 1.15 (0.5-3.9) | 6.6 (3.15-6.9) |
| Pain VAS (cm) | 7.55 (3.6-7.7) | 0.95 (0.2-1.05)* | 4.1 (0.5-6.55) |
| SF-36 Physical Health | 44.38 (42.5-47.5) | 50.63 (33.75-92.5) | 41.56 (35-69.4) |
| SF-36 Mental Health | 41.625 (28.5-57.8) | 75.88 (55-96) | 39.6 (37-57) |

The invention claimed is:

1. A method of treating, inhibiting, or ameliorating an autoinflammatory disorder, disease, or condition in a subject in need thereof, comprising administering to the subject a therapeutic amount of an interleukin 1 (IL-1) fusion protein antagonist once a week, wherein the autoinflammatory disorder, disease, or condition is treated, inhibited, or ameliorated, wherein the IL-1 fusion protein antagonist comprises two IL-1 receptor components and a multimerizing component comprising the amino acid sequence of SEQ ID NO:10, wherein the subject is a human adult or child diagnosed with Neonatal Onset Multisystem Inflammatory Disorder (NOMID/CINCA), Muckle-Wells Syndrome (MWS), Familial Cold Autoinflammatory Syndrome (FCAS), familial mediterranean fever (FMF), tumor necrosis factor receptor-associated periodic fever syndrome (TRAPS), or systemic onset juvenile idiopathic arthritis (Still's Disease).

2. The method of claim 1, wherein administration is subcutaneous, intramuscular, or intravenous.

3. The method of claim 1, wherein the therapeutically effective amount is between 1-20 mg/kg.

4. A method of treating, inhibiting, or ameliorating an autoinflammatory disorder associated with mutations in CIAS-1 in a subject in need thereof, comprising administering once a week to the subject a therapeutic amount of an interleukin 1 (IL-1) antagonist comprising the amino acid sequence of SEQ ID NO:10, wherein the autoinflammatory disorder is treated, inhibited, or ameliorated, and wherein the autoinflammatory disorder associated with mutations in CIAS-1 is one of Neonatal Onset Multisystem Inflammatory Disorder (NOMID/CINCA), Muckle-Wells Syndrome (MWS), and Familial Cold Autoinflammatory Syndrome (FCAS).

5. The method of claim 4, wherein administration is subcutaneous, intramuscular, or intravenous.

6. The method of claim 5, wherein the therapeutically effective amount is between 1-20 mg/kg.

* * * * *

SEQUENCE LISTING

<160> NUMBER OF SEQ ID NOS: 26

<210> SEQ ID NO 1
<211> LENGTH: 2733
<212> TYPE: DNA
<213> ORGANISM: Homo sapiens

<400> SEQUENCE: 1

```
atg gtg ctt ctg tgg tgt gta gtg agt ctc tac ttt tat gga atc ctg      48 caa agt gat gcc tca gaa cgc tgc gat gac tgg gga cta gac acc atg      96 agg caa atc caa gtg ttt gaa gat gag cca gct cgc atc aag tgc cca     144 ctc ttt gaa cac ttc ttg aaa ttc aac tac agc aca gcc cat tca gct     192 ggc ctt act ctg atc tgg tat tgg act agg cag gac cgg gac ctt gag     240 gag cca att aac ttc cgc ctc ccc gag aac cgc att agt aag gag aaa     288 gat gtg ctg tgg ttc cgg ccc act ctc ctc aat gac act ggc aac tat     336 acc tgc atg tta agg aac aca aca tat tgc agc aaa gtt gca ttt ccc     384 ttg gaa gtt gtt caa aaa gac agc tgt ttc aat tcc ccc atg aaa ctc     432
```

-continued

```
cca gtg cat aaa ctg tat ata gaa tat ggc att cag agg atc act tgt        480
cca aat gta gat gga tat ttt cct tcc agt gtc aaa ccg act atc act        528
tgg tat atg ggc tgt tat aaa ata cag aat ttt aat aat gta ata ccc        576
gaa ggt atg aac ttg agt ttc ctc att gcc tta att tca aat aat gga        624
aat tac aca tgt gtt gtt aca tat cca gaa aat gga cgt acg ttt cat        672
ctc acc agg act ctg act gta aag gta gta ggc tct cca aaa aat gca        720
gtg ccc cct gtg atc cat tca cct aat gat cat gtg gtc tat gag aaa        768
gaa cca gga gag gag cta ctc att ccc tgt acg gtc tat ttt agt ttt        816
ctg atg gat tct cgc aat gag gtt tgg tgg acc att gat gga aaa aaa        864
cct gat gac atc act att gat gtc acc att aac gaa agt ata agt cat        912
agt aga aca gaa gat gaa aca aga act cag att ttg agc atc aag aaa        960
gtt acc tct gag gat ctc aag cgc agc tat gtc tgt cat gct aga agt       1008
gcc aaa ggc gaa gtt gcc aaa gca gcc aag gtg aag cag aaa gtg cca       1056
gct cca aga tac aca gtg tcc ggt ggc gcg cct atg ctg agc gag gct       1104
gat aaa tgc aag gaa cgt gaa gaa aaa ata att tta gtg tca tct gca       1152
aat gaa att gat gtt cgt ccc tgt cct ctt aac cca aat gaa cac aaa       1200
ggc act ata act tgg tat aag gat gac agc aag aca cct gta tct aca       1248
gaa caa gcc tcc agg att cat caa cac aaa gag aaa ctt tgg ttt gtt       1296
cct gct aag gtg gag gat tca gga cat tac tat tgc gtg gta aga aat       1344
tca tct tac tgc ctc aga att aaa ata agt gca aaa ttt gtg gag aat       1392
gag cct aac tta tgt tat aat gca caa gcc ata ttt aag cag aaa cta       1440
ccc gtt gca gga gac gga gga ctt gtg tgc cct tat atg gag ttt ttt       1488
aaa aat gaa aat aat gag tta cct aaa tta cag tgg tat aag gat tgc       1536
aaa cct cta ctt ctt gac aat ata cac ttt agt gga gtc aaa gat agg       1584
ctc atc gtg atg aat gtg gct gaa aag cat aga ggg aac tat act tgt       1632
cat gca tcc tac aca tac ttg ggc aag caa tat cct att acc cgg gta       1680
ata gaa ttt att act cta gag gaa aac aaa ccc aca agg cct gtg att       1728
gtg agc cca gct aat gag aca atg gaa gta gac ttg gga tcc cag ata       1776
caa ttg atc tgt aat gtc acc ggc cag ttg agt gac att gct tac tgg       1824
aag tgg aat ggg tca gta att gat gaa gat gac cca gtg cta ggg gaa       1872
gac tat tac agt gtg gaa aat cct gca aac aaa aga agg agt acc ctc       1920
atc aca gtg ctt aat ata tcg gaa att gag agt aga ttt tat aaa cat       1968
cca ttt acc tgt ttt gcc aag aat aca cat ggt ata gat gca gca tat       2016
atc cag tta ata tat cca gtc act aat tcc gga gac aaa act cac aca       2064
tgc cca ccg tgc cca gca cct gaa ctc ctg ggg gga ccg tca gtc ttc       2112
ctc ttc ccc cca aaa ccc aag gac acc ctc atg atc tcc cgg acc cct       2160
gag gtc aca tgc gtg gtg gtg gac gtg agc cac gaa gac cct gag gtc       2208
aag ttc aac tgg tac gtg gac ggc gtg gag gtg cat aat gcc aag aca       2256
aag ccg cgg gag gag cag tac aac agc acg tac cgt gtg gtc agc gtc       2304
ctc acc gtc ctg cac cag gac tgg ctg aat ggc aag gag tac aag tgc       2352
```

```
aag gtc tcc aac aaa gcc ctc cca gcc ccc atc gag aaa acc atc tcc      2400 aaa gcc aaa ggg cag ccc cga gaa cca cag gtg tac acc ctg ccc cca      2448 tcc cgg gag gag atg acc aag aac cag gtc agc ctg acc tgc ctg gtc      2496 aaa ggc ttc tat ccc agc gac atc gcc gtg gag tgg gag agc aat ggg      2544 cag ccg gag aac aac tac aag acc acg cct ccc gtg ctg gac tcc gac      2592 ggc tcc ttc ttc ctc tat agc aag ctc acc gtg gac aag agc agg tgg      2640 cag cag ggg aac gtc ttc tca tgc tcc gtg atg cat gag gct ctg cac      2688 aac cac tac acg cag aag agc ctc tcc ctg tct ccg ggt aaa              2730 tga                                                                   2733
```

```
<210> SEQ ID NO 2
<211> LENGTH: 910
<212> TYPE: PRT
<213> ORGANISM: Homo sapiens

<400> SEQUENCE: 2
```

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285
```

-continued

```
Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Ser Gly Gly Ala Pro Met Leu Ser Glu Ala
        355                 360                 365

Asp Lys Cys Lys Glu Arg Glu Lys Ile Ile Leu Val Ser Ser Ala
    370                 375                 380

Asn Glu Ile Asp Val Arg Pro Cys Pro Leu Asn Pro Asn Glu His Lys
385                 390                 395                 400

Gly Thr Ile Thr Trp Tyr Lys Asp Asp Ser Lys Thr Pro Val Ser Thr
                405                 410                 415

Glu Gln Ala Ser Arg Ile His Gln His Lys Glu Lys Leu Trp Phe Val
                420                 425                 430

Pro Ala Lys Val Glu Asp Ser Gly His Tyr Tyr Cys Val Val Arg Asn
            435                 440                 445

Ser Ser Tyr Cys Leu Arg Ile Lys Ile Ser Ala Lys Phe Val Glu Asn
450                 455                 460

Glu Pro Asn Leu Cys Tyr Asn Ala Gln Ala Ile Phe Lys Gln Lys Leu
465                 470                 475                 480

Pro Val Ala Gly Asp Gly Gly Leu Val Cys Pro Tyr Met Glu Phe Phe
                485                 490                 495

Lys Asn Glu Asn Asn Glu Leu Pro Lys Leu Gln Trp Tyr Lys Asp Cys
                500                 505                 510

Lys Pro Leu Leu Leu Asp Asn Ile His Phe Ser Gly Val Lys Asp Arg
            515                 520                 525

Leu Ile Val Met Asn Val Ala Glu Lys His Arg Gly Asn Tyr Thr Cys
        530                 535                 540

His Ala Ser Tyr Thr Tyr Leu Gly Lys Gln Tyr Pro Ile Thr Arg Val
545                 550                 555                 560

Ile Glu Phe Ile Thr Leu Glu Glu Asn Lys Pro Thr Arg Pro Val Ile
                565                 570                 575

Val Ser Pro Ala Asn Glu Thr Met Glu Val Asp Leu Gly Ser Gln Ile
            580                 585                 590

Gln Leu Ile Cys Asn Val Thr Gly Gln Leu Ser Asp Ile Ala Tyr Trp
        595                 600                 605

Lys Trp Asn Gly Ser Val Ile Asp Glu Asp Pro Val Leu Gly Glu
    610                 615                 620

Asp Tyr Tyr Ser Val Glu Asn Pro Ala Asn Lys Arg Arg Ser Thr Leu
625                 630                 635                 640

Ile Thr Val Leu Asn Ile Ser Glu Ile Glu Ser Arg Phe Tyr Lys His
                645                 650                 655

Pro Phe Thr Cys Phe Ala Lys Asn Thr His Gly Ile Asp Ala Ala Tyr
            660                 665                 670

Ile Gln Leu Ile Tyr Pro Val Thr Asn Ser Gly Asp Lys Thr His Thr
        675                 680                 685

Cys Pro Pro Cys Pro Ala Pro Glu Leu Leu Gly Gly Pro Ser Val Phe
    690                 695                 700
```

-continued

```
Leu Phe Pro Pro Lys Pro Lys Asp Thr Leu Met Ile Ser Arg Thr Pro
705                 710                 715                 720

Glu Val Thr Cys Val Val Asp Val Ser His Glu Asp Pro Glu Val
            725                 730                 735

Lys Phe Asn Trp Tyr Val Asp Gly Val Glu Val His Asn Ala Lys Thr
        740                 745                 750

Lys Pro Arg Glu Glu Gln Tyr Asn Ser Thr Tyr Arg Val Val Ser Val
    755                 760                 765

Leu Thr Val Leu His Gln Asp Trp Leu Asn Gly Lys Glu Tyr Lys Cys
770                 775                 780

Lys Val Ser Asn Lys Ala Leu Pro Ala Pro Ile Glu Lys Thr Ile Ser
785                 790                 795                 800

Lys Ala Lys Gly Gln Pro Arg Glu Pro Gln Val Tyr Thr Leu Pro Pro
                805                 810                 815

Ser Arg Glu Glu Met Thr Lys Asn Gln Val Ser Leu Thr Cys Leu Val
            820                 825                 830

Lys Gly Phe Tyr Pro Ser Asp Ile Ala Val Glu Trp Glu Ser Asn Gly
        835                 840                 845

Gln Pro Glu Asn Asn Tyr Lys Thr Thr Pro Pro Val Leu Asp Ser Asp
    850                 855                 860

Gly Ser Phe Phe Leu Tyr Ser Lys Leu Thr Val Asp Lys Ser Arg Trp
865                 870                 875                 880

Gln Gln Gly Asn Val Phe Ser Cys Ser Val Met His Glu Ala Leu His
                885                 890                 895

Asn His Tyr Thr Gln Lys Ser Leu Ser Leu Ser Pro Gly Lys
            900                 905                 910

<210> SEQ ID NO 3
<211> LENGTH: 2703
<212> TYPE: DNA
<213> ORGANISM: Homo sapiens

<400> SEQUENCE: 3
atggtgttac tcagacttat ttgtttcata gctctactga tttcttctct ggaggctgat      60
aaatgcaagg aacgtgaaga aaaataatt ttagtgtcat ctgcaaatga aattgatgtt     120
cgtccctgtc ctcttaaccc aaatgaacac aaaggcacta acttggta taaggatgac      180 agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aatttgtgg agaatgagcc taacttatgt      360
tataatgcac aagccatatt taagcagaaa ctacccgttg caggagacgg aggacttgtg     420
tgcccttata tggagttttt taaaaatgaa ataatgagt tacctaaatt acagtggtat      480
aaggattgca aacctctact tcttgacaat atacactta gtggagtcaa agataggctc      540
atcgtgatga atgtggctga aaagcataga gggaactata cttgtcatgc atcctacaca     600
tacttgggca gcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactgaag      780 tggaatgggt cagtaattga tgaagatgac ccagtgctag gggaagacta ttacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
```

```
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga gaaagatgtg ctgtggttcc ggcccactct cctcaatgac    1260
actggcaact ataccctgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atattttcct    1440
tccagtgtca aaccgactat cacttggtat atgggctgtt ataaaataca gaattttaat    1500
aatgtaatac ccgaaggtat gaacttgagt ttcctcattg ccttaatttc aaataatgga    1560
aattacacat gtgttgttac atatccagaa aatggacgta cgtttcatct caccaggact    1620
ctgactgtaa aggtagtagg ctctccaaaa aatgcagtgc ccctgtgat ccattcacct    1680 aatgatcatg tggtctatga gaaagaacca ggagaggagc tactcattcc ctgtacggtc    1740
tattttagtt ttctgatgga ttctcgcaat gaggtttggt ggaccattga tggaaaaaaa    1800
cctgatgaca tcactattga tgtcaccatt aacgaaagta taagtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg gaatccggag acaaaactca cacatgccca    2040
ccgtgcccag cacctgaact cctgggggga ccgtcagtct tcctcttccc cccaaaaccc    2100
aaggacaccc tcatgatctc ccggacccct gaggtcacat gcgtggtggt ggacgtgagc    2160
cacgaagacc ctgaggtcaa gttcaactgg tacgtggacg gcgtggaggt gcataatgcc    2220
aagacaaagc cgcggaggga gcagtacaac agcacgtacc gtgtggtcag cgtcctcacc    2280
gtcctgcacc aggactggct gaatggcaag gagtacaagt gcaaggtctc caacaaagcc    2340
ctcccagccc ccatcgagaa aaccatctcc aaagccaaag gcagccccg agaaccacag    2400 gtgtacaccc tgcccccatc ccgggaggag atgaccaaga accaggtcag cctgacctgc    2460
ctggtcaaag gcttctatcc cagcgacatc gccgtggagt gggagagcaa tgggcagccg    2520
gagaacaact acaagaccac gcctcccgtg ctggactccg acggctcctt cttcctctat    2580
agcaagctca ccgtggacaa gagcaggtgg cagcagggga acgtcttctc atgctccgtg    2640
atgcatgagg ctctgcacaa ccactacacg cagaagagcc tctccctgtc tccgggtaaa    2700
tga                                                                 2703
```

<210> SEQ ID NO 4
<211> LENGTH: 900
<212> TYPE: PRT
<213> ORGANISM: Homo sapiens

<400> SEQUENCE: 4

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

-continued

Val Ser Thr Glu Gln Ala Ser Arg Ile His Gln His Lys Glu Lys Leu
65              70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
    290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

```
Ser Ser Val Lys Pro Thr Ile Thr Trp Tyr Met Gly Cys Tyr Lys Ile
            485             490                 495

Gln Asn Phe Asn Asn Val Ile Pro Glu Gly Met Asn Leu Ser Phe Leu
            500             505                 510

Ile Ala Leu Ile Ser Asn Asn Gly Asn Tyr Thr Cys Val Val Thr Tyr
            515             520                 525

Pro Glu Asn Gly Arg Thr Phe His Leu Thr Arg Thr Leu Thr Val Lys
            530             535                 540

Val Val Gly Ser Pro Lys Asn Ala Val Pro Pro Val Ile His Ser Pro
545             550             555                 560

Asn Asp His Val Val Tyr Glu Lys Glu Pro Gly Glu Glu Leu Leu Ile
                565             570                 575

Pro Cys Thr Val Tyr Phe Ser Phe Leu Met Asp Ser Arg Asn Glu Val
            580             585                 590

Trp Trp Thr Ile Asp Gly Lys Lys Pro Asp Asp Ile Thr Ile Asp Val
            595             600                 605

Thr Ile Asn Glu Ser Ile Ser His Ser Arg Thr Glu Asp Glu Thr Arg
            610             615                 620

Thr Gln Ile Leu Ser Ile Lys Lys Val Thr Ser Glu Asp Leu Lys Arg
625             630             635                 640

Ser Tyr Val Cys His Ala Arg Ser Ala Lys Gly Glu Val Ala Lys Ala
                645             650                 655

Ala Lys Val Lys Gln Lys Val Pro Ala Pro Arg Tyr Thr Val Glu Ser
            660             665                 670

Gly Asp Lys Thr His Thr Cys Pro Pro Cys Pro Ala Pro Glu Leu Leu
            675             680                 685

Gly Gly Pro Ser Val Phe Leu Phe Pro Pro Lys Pro Lys Asp Thr Leu
            690             695                 700

Met Ile Ser Arg Thr Pro Glu Val Thr Cys Val Val Val Asp Val Ser
705             710             715                 720

His Glu Asp Pro Glu Val Lys Phe Asn Trp Tyr Val Asp Gly Val Glu
                725             730                 735

Val His Asn Ala Lys Thr Lys Pro Arg Glu Glu Gln Tyr Asn Ser Thr
            740             745                 750

Tyr Arg Val Val Ser Val Leu Thr Val Leu His Gln Asp Trp Leu Asn
            755             760                 765

Gly Lys Glu Tyr Lys Cys Lys Val Ser Asn Lys Ala Leu Pro Ala Pro
            770             775                 780

Ile Glu Lys Thr Ile Ser Lys Ala Lys Gly Gln Pro Arg Glu Pro Gln
785             790             795                 800

Val Tyr Thr Leu Pro Pro Ser Arg Glu Glu Met Thr Lys Asn Gln Val
                805             810                 815

Ser Leu Thr Cys Leu Val Lys Gly Phe Tyr Pro Ser Asp Ile Ala Val
            820             825                 830

Glu Trp Glu Ser Asn Gly Gln Pro Glu Asn Asn Tyr Lys Thr Thr Pro
            835             840                 845

Pro Val Leu Asp Ser Asp Gly Ser Phe Phe Leu Tyr Ser Lys Leu Thr
            850             855                 860

Val Asp Lys Ser Arg Trp Gln Gln Gly Asn Val Phe Ser Cys Ser Val
865             870             875                 880

Met His Glu Ala Leu His Asn His Tyr Thr Gln Lys Ser Leu Ser Leu
                885             890                 895

Ser Pro Gly Lys
```

<210> SEQ ID NO 5
<211> LENGTH: 2709
<212> TYPE: DNA
<213> ORGANISM: Homo sapiens

<400> SEQUENCE: 5

```
atggtgttac tcagacttat ttgtttcata gctctactga tttcttctct ggaggctgat      60
aaatgcaagg aacgtgaaga aaaaataatt ttagtgtcat ctgcaaatga aattgatgtt     120
cgtccctgtc ctcttaaccc aaatgaacac aaaggcacta aacttggta taaggatgac     180
agcaagacac ctgtatctac agaacaagcc tccaggattc atcaacacaa agagaaactt     240
tggtttgttc ctgctaaggt ggaggattca ggacattact attgcgtggt aagaaattca     300
tcttactgcc tcagaattaa aataagtgca aaatttgtgg agaatgagcc taacttatgt     360
tataatgcac aagccatatt taagcagaaa ctacccgttg caggagacgg aggacttgtg     420
tgccctttata tggagttttt taaaaatgaa ataatgagt tacctaaatt acagtggtat     480
aaggattgca aacctctact tcttgacaat atacactttta gtggagtcaa agataggctc     540
atcgtgatga atgtggctga aaagcataga gggaactata cttgtcatgc atcctacaca     600
tacttgggca gcaatatcc tattacccgg gtaatagaat ttattactct agaggaaaac     660
aaacccacaa ggcctgtgat tgtgagccca gctaatgaga caatggaagt agacttggga     720
tcccagatac aattgatctg taatgtcacc ggccagttga gtgacattgc ttactggaag     780
tggaatgggt cagtaattga tgaagatgac ccagtgctag ggaagactact tacagtgtg     840
gaaaatcctg caaacaaaag aaggagtacc ctcatcacag tgcttaatat atcggaaatt     900
gagagtagat tttataaaca tccatttacc tgttttgcca agaatacaca tggtatagat     960
gcagcatata tccagttaat atatccagtc actaattcag aacgctgcga tgactgggga    1020
ctagacacca tgaggcaaat ccaagtgttt gaagatgagc cagctcgcat caagtgccca    1080
ctctttgaac acttcttgaa attcaactac agcacagccc attcagctgg ccttactctg    1140
atctggtatt ggactaggca ggaccgggac cttgaggagc caattaactt ccgcctcccc    1200
gagaaccgca ttagtaagga aaagatgtg ctgtggttcc ggcccactct cctcaatgac    1260
actggcaact ataccctgcat gttaaggaac actacatatt gcagcaaagt tgcatttccc    1320
ttggaagttg ttcaaaaaga cagctgtttc aattcccca tgaaactccc agtgcataaa    1380
ctgtatatag aatatggcat tcagaggatc acttgtccaa atgtagatgg atatttttcct    1440
tccagtgtca aaccgactat cacttggtat atgggctgtt ataaaatca gaatttttaat    1500
aatgtaatac ccgaaggtat gaacttgagt ttcctcattg ccttaatttc aaataatgga    1560
aattacacat gtgttgttac atatccagaa aatggacgta cgtttcatct caccaggact    1620
ctgactgtaa aggtagtagg ctctccaaaa aatgcagtgc ccctgtgat ccattcacct    1680
aatgatcatg tggtctatga aaagaaccaa ggagaggagc tactcattcc ctgtacggtc    1740
tatttttagtt ttctgatgga ttctcgcaat gaggtttggt ggaccattga tggaaaaaaa    1800
cctgatgaca tcactattga tgtcaccatt aacgaaagta agtcatag tagaacagaa    1860
gatgaaacaa gaactcagat tttgagcatc aagaaagtta cctctgagga tctcaagcgc    1920
agctatgtct gtcatgctag aagtgccaaa ggcgaagttg ccaaagcagc caaggtgaag    1980
cagaaagtgc cagctccaag atacacagtg aatccggag agtccaaata cggtccgcca    2040
tgcccatcat gcccagcacc tgagttcctg gggggaccat cagtcttcct gttccccca    2100
```

-continued

```
aaacccaagg acactctcat gatctcccgg accccctgagg tcacgtgcgt ggtggtggac    2160
gtgagccagg aagaccccga ggtccagttc aactggtacg tggatggcgt ggaggtgcat    2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaagggca gccccgagag    2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga acaactacaa gaccacgcct cccgtgctgg actccgacgg ctccttcttc    2580
ctctacagca agctaaccgt ggacaagagc aggtggcagg aggggaatgt cttctcatgc    2640
tccgtgatgc atgaggctct gcacaaccac tacacacaga agagcctctc cctgtctctg    2700
ggtaaatga                                                            2709
```

<210> SEQ ID NO 6
<211> LENGTH: 902
<212> TYPE: PRT
<213> ORGANISM: Homo sapiens

<400> SEQUENCE: 6

```
Met Val Leu Leu Arg Leu Ile Cys Phe Ile Ala Leu Leu Ile Ser Ser
 1               5                  10                  15

Leu Glu Ala Asp Lys Cys Lys Glu Arg Glu Glu Lys Ile Ile Leu Val
            20                  25                  30

Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
            100                 105                 110

Val Glu Asn Glu Pro Asn Leu Cys Tyr Asn Ala Gln Ala Ile Phe Lys
        115                 120                 125

Gln Lys Leu Pro Val Ala Gly Asp Gly Gly Leu Val Cys Pro Tyr Met
    130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
            180                 185                 190

Tyr Thr Cys His Ala Ser Tyr Thr Tyr Leu Gly Lys Gln Tyr Pro Ile
        195                 200                 205

Thr Arg Val Ile Glu Phe Ile Thr Leu Glu Glu Asn Lys Pro Thr Arg
    210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255
```

```
Ala Tyr Trp Lys Trp Asn Gly Ser Val Ile Asp Glu Asp Pro Val
            260                 265                 270

Leu Gly Glu Asp Tyr Tyr Ser Val Glu Asn Pro Ala Asn Lys Arg Arg
        275                 280                 285

Ser Thr Leu Ile Thr Val Leu Asn Ile Ser Glu Ile Glu Ser Arg Phe
        290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
            340                 345                 350

Glu Pro Ala Arg Ile Lys Cys Pro Leu Phe Glu His Phe Leu Lys Phe
        355                 360                 365

Asn Tyr Ser Thr Ala His Ser Ala Gly Leu Thr Leu Ile Trp Tyr Trp
    370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
            420                 425                 430

Tyr Cys Ser Lys Val Ala Phe Pro Leu Glu Val Val Gln Lys Asp Ser
        435                 440                 445

Cys Phe Asn Ser Pro Met Lys Leu Pro Val His Lys Leu Tyr Ile Glu
    450                 455                 460

Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
            500                 505                 510

Ile Ala Leu Ile Ser Asn Asn Gly Asn Tyr Thr Cys Val Val Thr Tyr
        515                 520                 525

Pro Glu Asn Gly Arg Thr Phe His Leu Thr Arg Thr Leu Thr Val Lys
    530                 535                 540

Val Val Gly Ser Pro Lys Asn Ala Val Pro Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
            580                 585                 590

Trp Trp Thr Ile Asp Gly Lys Lys Pro Asp Asp Ile Thr Ile Asp Val
        595                 600                 605

Thr Ile Asn Glu Ser Ile Ser His Ser Arg Thr Glu Asp Glu Thr Arg
    610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
            660                 665                 670

Gly Glu Ser Lys Tyr Gly Pro Pro Cys Pro Ser Cys Pro Ala Pro Glu
```

```
                675              680              685
Phe Leu Gly Gly Pro Ser Val Phe Leu Phe Pro Lys Pro Lys Asp
    690              695              700
Thr Leu Met Ile Ser Arg Thr Pro Glu Val Thr Cys Val Val Asp
705              710              715              720
Val Ser Gln Glu Asp Pro Glu Val Gln Phe Asn Trp Tyr Val Asp Gly
                725              730              735
Val Glu Val His Asn Ala Lys Thr Lys Pro Arg Glu Gln Phe Asn
            740              745              750
Ser Thr Tyr Arg Val Val Ser Val Leu Thr Val Leu His Gln Asp Trp
                755              760              765
Leu Asn Gly Lys Glu Tyr Lys Cys Lys Val Ser Asn Lys Gly Leu Pro
    770              775              780
Ser Ser Ile Glu Lys Thr Ile Ser Lys Ala Lys Gly Gln Pro Arg Glu
785              790              795              800
Pro Gln Val Tyr Thr Leu Pro Pro Ser Gln Glu Glu Met Thr Lys Asn
                805              810              815
Gln Val Ser Leu Thr Cys Leu Val Lys Gly Phe Tyr Pro Ser Asp Ile
            820              825              830
Ala Val Glu Trp Glu Ser Asn Gly Gln Pro Glu Asn Asn Tyr Lys Thr
                835              840              845
Thr Pro Pro Val Leu Asp Ser Asp Gly Ser Phe Phe Leu Tyr Ser Arg
    850              855              860
Leu Thr Val Asp Lys Ser Arg Trp Gln Glu Gly Asn Val Phe Ser Cys
865              870              875              880
Ser Val Met His Glu Ala Leu His Asn His Tyr Thr Gln Lys Ser Leu
                885              890              895
Ser Leu Ser Leu Gly Lys
            900

<210> SEQ ID NO 7
<211> LENGTH: 2709
<212> TYPE: DNA
<213> ORGANISM: Homo sapiens

<400> SEQUENCE: 7
atggtgttac tcagacttat ttgtttcata gctctactga tttcttctct ggaggctgat    60
aaatgcaagg aacgtgaaga aaaataatt ttagtgtcat ctgcaaatga aattgatgtt   120
cgtccctgtc ctcttaaccc aaatgaacac aaaggcacta aacttggta taaggatgac   180 agcaagacac ctgtatctac agaacaagcc tccaggattc atcaacacaa agagaaactt   240
tggtttgttc ctgctaaggt ggaggattca ggacattact attgcgtggt aagaaattca   300
tcttactgcc tcagaattaa aataagtgca aatttgtgg agaatgagcc taacttatgt   360
tataatgcac aagccatatt taagcagaaa ctacccgttg caggagacgg aggacttgtg   420 tgccctttata tggagttttt taaaaatgaa ataatgagt tacctaaatt acagtggtat   480
aaggattgca aacctctact tcttgacaat atacacttta gtggagtcaa agataggctc   540
atcgtgatga atgtggctga aaagcataga gggaactata cttgtcatgc atcctacaca   600
tacttgggca gcaatatcc tattacccgg gtaatagaat ttattactct agaggaaaac   660
aaacccacaa ggcctgtgat tgtgagccca gctaatgaga caatggaagt agacttggga   720
tcccagatac aattgatctg taatgtcacc ggccagttga gtgacattgc ttactggaag   780
tggaatgggt cagtaattga tgaagatgac ccagtgctag gggaagacta ttacagtgtg   840
```

-continued

```
gaaaatcctg caaacaaaag aaggagtacc ctcatcacag tgcttaatat atcggaaatt      900
gagagtagat tttataaaca tccatttacc tgttttgcca agaatacaca tggtatagat      960
gcagcatata tccagttaat atatccagtc actaattcag aacgctgcga tgactgggga     1020
ctagacacca tgaggcaaat ccaagtgttt gaagatgagc cagctcgcat caagtgccca     1080
ctctttgaac acttcttgaa attcaactac agcacagccc attcagctgg ccttactctg     1140
atctggtatt ggactaggca ggaccgggac cttgaggagc caattaactt ccgcctcccc     1200
gagaaccgca ttagtaagga aaagatgtg ctgtggttcc ggcccactct cctcaatgac      1260
actggcaact ataccctgcat gttaaggaac actacatatt gcagcaaagt tgcatttccc    1320
ttggaagttg ttcaaaaaga cagctgtttc aattccccca tgaaactccc agtgcataaa    1380
ctgtatatag aatatggcat tcagaggatc acttgtccaa atgtagatgg atattttcct     1440
tccagtgtca aaccgactat cacttggtat atgggctgtt ataaaataca gaattttaat     1500
aatgtaatac ccgaaggtat gaacttgagt ttcctcattg ccttaatttc aaataatgga     1560
aattacacat gtgttgttac atatccagaa aatggacgta cgtttcatct caccaggact    1620
ctgactgtaa aggtagtagg ctctccaaaa aatgcagtgc ccctgtgat ccattcacct      1680
aatgatcatg tggtctatga aaagaaacca ggagaggagc tactcattcc ctgtacggtc     1740
tattttagtt ttctgatgga ttctcgcaat gaggtttggt ggaccattga tggaaaaaaa     1800
cctgatgaca tcactattga tgtcaccatt aacgaaagta taagtcatag tagaacagaa     1860
gatgaaacaa gaactcagat tttgagcatc aagaaagtta cctctgagga tctcaagcgc     1920
agctatgtct gtcatgctag aagtgccaaa ggcgaagttg ccaaagcagc caaggtgaag    1980
cagaaagtgc cagctccaag atacacatg gaatccggag agtccaaata cggtccgcca      2040
tgcccaccat gcccagcacc tgagttcctg gggggaccat cagtcttcct gttccccca      2100
aaacccaagg acactctcat gatctcccgg accctgagg tcacgtgcgt ggtggtggac     2160
gtgagccagg aagaccccga ggtccagttc aactggtacg tggatggcgt ggaggtgcat     2220
aatgccaaga caaagccgcg ggaggagcag ttcaacagca cgtaccgtgt ggtcagcgtc    2280
ctcaccgtcc tgcaccagga ctggctgaac ggcaaggagt acaagtgcaa ggtctccaac    2340
aaaggcctcc cgtcctccat cgagaaaacc atctccaaag ccaaaggca gccccgagag     2400
ccacaggtgt acaccctgcc cccatcccag gaggagatga ccaagaacca ggtcagcctg    2460
acctgcctgg tcaaaggctt ctaccccagc gacatcgccg tggagtggga gagcaatggg    2520
cagccggaga caactacaa gaccacgcct cccgtgctgg actccgacgg ctccttcttc     2580
ctctacagca ggctaaccgt ggacaagagc aggtggcagg aggggaatgt cttctcatgc    2640
tccgtgatgc atgaggctct gcacaaccac tacacacaga gagcctctc cctgtctctg     2700
ggtaaatga                                                              2709
```

<210> SEQ ID NO 8
<211> LENGTH: 902
<212> TYPE: PRT
<213> ORGANISM: Homo sapiens

<400> SEQUENCE: 8

Met Val Leu Leu Arg Leu Ile Cys Phe Ile Ala Leu Leu Ile Ser Ser
1               5                   10                  15

Leu Glu Ala Asp Lys Cys Lys Glu Arg Glu Glu Lys Ile Ile Leu Val
            20                  25                  30

```
Ser Ser Ala Asn Glu Ile Asp Val Arg Pro Cys Pro Leu Asn Pro Asn
        35                  40                  45

Glu His Lys Gly Thr Ile Thr Trp Tyr Lys Asp Asp Ser Lys Thr Pro
    50                  55                  60

Val Ser Thr Glu Gln Ala Ser Arg Ile His Gln His Lys Glu Lys Leu
65                  70                  75                  80

Trp Phe Val Pro Ala Lys Val Glu Asp Ser Gly His Tyr Tyr Cys Val
                85                  90                  95

Val Arg Asn Ser Ser Tyr Cys Leu Arg Ile Lys Ile Ser Ala Lys Phe
                100                 105                 110

Val Glu Asn Glu Pro Asn Leu Cys Tyr Asn Ala Gln Ala Ile Phe Lys
            115                 120                 125

Gln Lys Leu Pro Val Ala Gly Asp Gly Gly Leu Val Cys Pro Tyr Met
        130                 135                 140

Glu Phe Phe Lys Asn Glu Asn Asn Glu Leu Pro Lys Leu Gln Trp Tyr
145                 150                 155                 160

Lys Asp Cys Lys Pro Leu Leu Leu Asp Asn Ile His Phe Ser Gly Val
                165                 170                 175

Lys Asp Arg Leu Ile Val Met Asn Val Ala Glu Lys His Arg Gly Asn
                180                 185                 190

Tyr Thr Cys His Ala Ser Tyr Thr Tyr Leu Gly Lys Gln Tyr Pro Ile
            195                 200                 205

Thr Arg Val Ile Glu Phe Ile Thr Leu Glu Glu Asn Lys Pro Thr Arg
        210                 215                 220

Pro Val Ile Val Ser Pro Ala Asn Glu Thr Met Glu Val Asp Leu Gly
225                 230                 235                 240

Ser Gln Ile Gln Leu Ile Cys Asn Val Thr Gly Gln Leu Ser Asp Ile
                245                 250                 255

Ala Tyr Trp Lys Trp Asn Gly Ser Val Ile Asp Glu Asp Asp Pro Val
                260                 265                 270

Leu Gly Glu Asp Tyr Tyr Ser Val Glu Asn Pro Ala Asn Lys Arg Arg
            275                 280                 285

Ser Thr Leu Ile Thr Val Leu Asn Ile Ser Glu Ile Glu Ser Arg Phe
        290                 295                 300

Tyr Lys His Pro Phe Thr Cys Phe Ala Lys Asn Thr His Gly Ile Asp
305                 310                 315                 320

Ala Ala Tyr Ile Gln Leu Ile Tyr Pro Val Thr Asn Ser Glu Arg Cys
                325                 330                 335

Asp Asp Trp Gly Leu Asp Thr Met Arg Gln Ile Gln Val Phe Glu Asp
                340                 345                 350

Glu Pro Ala Arg Ile Lys Cys Pro Leu Phe Glu His Phe Leu Lys Phe
            355                 360                 365

Asn Tyr Ser Thr Ala His Ser Ala Gly Leu Thr Leu Ile Trp Tyr Trp
        370                 375                 380

Thr Arg Gln Asp Arg Asp Leu Glu Glu Pro Ile Asn Phe Arg Leu Pro
385                 390                 395                 400

Glu Asn Arg Ile Ser Lys Glu Lys Asp Val Leu Trp Phe Arg Pro Thr
                405                 410                 415

Leu Leu Asn Asp Thr Gly Asn Tyr Thr Cys Met Leu Arg Asn Thr Thr
                420                 425                 430

Tyr Cys Ser Lys Val Ala Phe Pro Leu Glu Val Val Gln Lys Asp Ser
            435                 440                 445

Cys Phe Asn Ser Pro Met Lys Leu Pro Val His Lys Leu Tyr Ile Glu
```

```
            450                 455                 460
Tyr Gly Ile Gln Arg Ile Thr Cys Pro Asn Val Asp Gly Tyr Phe Pro
465                 470                 475                 480

Ser Ser Val Lys Pro Thr Ile Thr Trp Tyr Met Gly Cys Tyr Lys Ile
                485                 490                 495

Gln Asn Phe Asn Asn Val Ile Pro Glu Gly Met Asn Leu Ser Phe Leu
                500                 505                 510

Ile Ala Leu Ile Ser Asn Asn Gly Asn Tyr Thr Cys Val Val Thr Tyr
                515                 520                 525

Pro Glu Asn Gly Arg Thr Phe His Leu Thr Arg Thr Leu Thr Val Lys
530                 535                 540

Val Val Gly Ser Pro Lys Asn Ala Val Pro Val Ile His Ser Pro
545                 550                 555                 560

Asn Asp His Val Val Tyr Glu Lys Glu Pro Gly Glu Glu Leu Leu Ile
                565                 570                 575

Pro Cys Thr Val Tyr Phe Ser Phe Leu Met Asp Ser Arg Asn Glu Val
                580                 585                 590

Trp Trp Thr Ile Asp Gly Lys Lys Pro Asp Asp Ile Thr Ile Asp Val
                595                 600                 605

Thr Ile Asn Glu Ser Ile Ser His Ser Arg Thr Glu Asp Glu Thr Arg
                610                 615                 620

Thr Gln Ile Leu Ser Ile Lys Lys Val Thr Ser Glu Asp Leu Lys Arg
625                 630                 635                 640

Ser Tyr Val Cys His Ala Arg Ser Ala Lys Gly Glu Val Ala Lys Ala
                645                 650                 655

Ala Lys Val Lys Gln Lys Val Pro Ala Pro Arg Tyr Thr Val Glu Ser
                660                 665                 670

Gly Glu Ser Lys Tyr Gly Pro Pro Cys Pro Pro Cys Pro Ala Pro Glu
                675                 680                 685

Phe Leu Gly Gly Pro Ser Val Phe Leu Phe Pro Pro Lys Pro Lys Asp
                690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
                725                 730                 735

Val Glu Val His Asn Ala Lys Thr Lys Pro Arg Glu Glu Gln Phe Asn
                740                 745                 750

Ser Thr Tyr Arg Val Val Ser Val Leu Thr Val Leu His Gln Asp Trp
                755                 760                 765

Leu Asn Gly Lys Glu Tyr Lys Cys Lys Val Ser Asn Lys Gly Leu Pro
                770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Met Thr Lys Asn
                805                 810                 815

Gln Val Ser Leu Thr Cys Leu Val Lys Gly Phe Tyr Pro Ser Asp Ile
                820                 825                 830

Ala Val Glu Trp Glu Ser Asn Gly Gln Pro Glu Asn Asn Tyr Lys Thr
                835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880
```

Ser Val Met His Glu Ala Leu His Asn His Tyr Thr Gln Lys Ser Leu
            885                 890                 895

Ser Leu Ser Leu Gly Lys
        900

<210> SEQ ID NO 9
<211> LENGTH: 2703
<212> TYPE: DNA
<213> ORGANISM: Homo sapiens

<400> SEQUENCE: 9

| | | | | | |
|---|---|---|---|---|---|
| atggtgcttc | tgtggtgtgt | agtgagtctc | tacttttatg | gaatcctgca | aagtgatgcc | 60 |
| tcagaacgct | gcgatgactg | gggactagac | accatgaggc | aaatccaagt | gtttgaagat | 120 |
| gagccagctc | gcatcaagtg | cccactcttt | gaacacttct | tgaaattcaa | ctacagcaca | 180 |
| gcccattcag | ctggccttac | tctgatctgg | tattggacta | gcaggaccg | ggaccttgag | 240 |
| gagccaatta | acttccgcct | ccccgagaac | cgcattagta | aggagaaaga | tgtgctgtgg | 300 |
| ttccggccca | ctctcctcaa | tgacactggc | aactatacct | gcatgttaag | gaacactaca | 360 |
| tattgcagca | aagttgcatt | tcccttggaa | gttgttcaaa | aagacagctg | tttcaattcc | 420 |
| cccatgaaac | tcccagtgca | taaactgtat | atagaatatg | gcattcagag | gatcacttgt | 480 |
| ccaaatgtag | atggatattt | tccttccagt | gtcaaaccga | ctatcacttg | gtatatgggc | 540 |
| tgttataaaa | tacagaattt | taataatgta | atacccgaag | gtatgaactt | gagtttcctc | 600 |
| attgccttaa | tttcaaataa | tggaaattac | acatgtgttg | ttacatatcc | agaaaatgga | 660 |
| cgtacgtttc | atctcaccag | gactctgact | gtaaaggtag | taggctctcc | aaaaaatgca | 720 |
| gtgccccctg | tgatccattc | acctaatgat | catgtggtct | atgagaaaga | accaggagag | 780 |
| gagctactca | ttccctgtac | ggtctatttt | agttttctga | tggattctcg | caatgaggtt | 840 |
| tggtggacca | ttgatggaaa | aaacctgat | gacatcacta | ttgatgtcac | cattaacgaa | 900 |
| agtataagtc | atagtagaac | agaagatgaa | acaagaactc | agattttgag | catcaagaaa | 960 |
| gttacctctg | aggatctcaa | gcgcagctat | gtctgtcatg | ctagaagtgc | caaggcgaa | 1020 |
| gttgccaaag | cagccaaggt | gaagcagaaa | gtgccagctc | caagatacac | agtggaaaaa | 1080 |
| tgcaaggaac | gtgaagaaaa | aataattta | gtgagctcag | caaatgaaat | cgatgttcgt | 1140 |
| ccctgtcctc | ttaacccaaa | tgaacacaaa | ggcactataa | cttggtataa | ggatgacagc | 1200 |
| aagacacctg | tatctacaga | acaagcctcc | aggattcatc | aacacaaaga | gaaactttgg | 1260 |
| tttgttcctg | ctaaggtgga | ggattcagga | cattactatt | gcgtggtaag | aaattcatct | 1320 |
| tactgcctca | gaattaaaat | aagtgcaaaa | tttgtggaga | atgagcctaa | cttatgttat | 1380 |
| aatgcacaag | ccatatttaa | gcagaaacta | cccgttgcag | agacggagg | acttgtgtgc | 1440 |
| ccttatatgg | agtttttaa | aaatgaaaat | aatgagttac | ctaaattaca | gtggtataag | 1500 |
| gattgcaaac | tctctacttct | tgacaatata | cactttagtg | gagtcaaaga | taggctcatc | 1560 |
| gtgatgaatg | tggctgaaaa | gcatagaggg | aactatactt | gtcatgcatc | ctacacatac | 1620 |
| ttgggcaagc | aatatcctat | tacccgggta | atagaattta | ttactctaga | ggaaaacaaa | 1680 |
| cccacaaggc | ctgtgattgt | gagcccagct | aatgagacaa | tggaagtaga | cttgggatcc | 1740 |
| cagatacaat | tgatctgtaa | tgtcaccggc | cagttgagtg | acattgctta | ctggaagtgg | 1800 |
| aatgggtcag | taattgatga | agatgaccca | gtgctagggg | aagactatta | cagtgtggaa | 1860 |
| aatcctgcaa | acaaaagaag | gagtaccctc | atcacagtgc | ttaatatatc | ggaaattgag | 1920 |

```
agtagatttt ataaacatcc atttacctgt tttgccaaga atacacatgg tatagatgca   1980
gcatatatcc agttaatata tccagtcact aattccggag acaaaactca cacatgccca   2040
ccgtgcccag cacctgaact cctgggggga ccgtcagtct tcctcttccc cccaaaaccc   2100
aaggacaccc tcatgatctc ccggaccoct gaggtcacat gcgtggtggt ggacgtgagc   2160
cacgaagacc ctgaggtcaa gttcaactgg tacgtggacg gcgtggaggt gcataatgcc   2220
aagacaaagc cgcgggagga gcagtacaac agcacgtacc gtgtggtcag cgtcctcacc   2280
gtcctgcacc aggactggct gaatggcaag gagtacaagt gcaaggtctc caacaaagcc   2340
ctcccagccc ccatcgagaa aaccatctcc aaagccaaag gcagccccg agaaccacag   2400
gtgtacaccc tgccccatc ccgggatgag ctgaccaaga accaggtcag cctgacctgc   2460
ctggtcaaag gcttctatcc cagcgacatc gccgtggagt gggagagcaa tgggcagccg   2520
gagaacaact acaagaccac gcctcccgtg ctggactccg acggctcctt cttcctctac   2580
agcaagctca ccgtggacaa gagcaggtgg cagcagggga acgtcttctc atgctccgtg   2640
atgcatgagg ctctgcacaa ccactacacg cagaagagcc tctccctgtc tccgggtaaa   2700
tga                                                                2703
```

<210> SEQ ID NO 10
<211> LENGTH: 900
<212> TYPE: PRT
<213> ORGANISM: Homo sapiens

<400> SEQUENCE: 10

| Met | Val | Leu | Leu | Trp | Cys | Val | Val | Ser | Leu | Tyr | Phe | Tyr | Gly | Ile | Leu |
|---|---|---|---|---|---|---|---|---|---|---|---|---|---|---|---|
| 1 | | | | 5 | | | | | 10 | | | | | 15 | |

| Gln | Ser | Asp | Ala | Ser | Glu | Arg | Cys | Asp | Asp | Trp | Gly | Leu | Asp | Thr | Met |
| | | | 20 | | | | | 25 | | | | | 30 | | |

| Arg | Gln | Ile | Gln | Val | Phe | Glu | Asp | Glu | Pro | Ala | Arg | Ile | Lys | Cys | Pro |
| | | 35 | | | | | 40 | | | | | 45 | | | |

Leu Phe Glu His Phe Leu Lys Phe Asn Tyr Ser Thr Ala His Ser Ala
50              55                  60

Gly Leu Thr Leu Ile Trp Tyr Trp Thr Arg Gln Asp Arg Asp Leu Glu
65              70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala

-continued

```
            225                 230                 235                 240
Val Pro Pro Val Ile His Ser Pro Asn Asp His Val Val Tyr Glu Lys
                245                 250                 255
Glu Pro Gly Glu Glu Leu Leu Ile Pro Cys Thr Val Tyr Phe Ser Phe
                260                 265                 270
Leu Met Asp Ser Arg Asn Glu Val Trp Trp Thr Ile Asp Gly Lys Lys
            275                 280                 285
Pro Asp Asp Ile Thr Ile Asp Val Thr Ile Asn Glu Ser Ile Ser His
            290                 295                 300
Ser Arg Thr Glu Asp Glu Thr Arg Thr Gln Ile Leu Ser Ile Lys Lys
305                 310                 315                 320
Val Thr Ser Glu Asp Leu Lys Arg Ser Tyr Val Cys His Ala Arg Ser
                325                 330                 335
Ala Lys Gly Glu Val Ala Lys Ala Ala Lys Val Lys Gln Lys Val Pro
                340                 345                 350
Ala Pro Arg Tyr Thr Val Glu Lys Cys Lys Glu Arg Glu Glu Lys Ile
                355                 360                 365
Ile Leu Val Ser Ser Ala Asn Glu Ile Asp Val Arg Pro Cys Pro Leu
            370                 375                 380
Asn Pro Asn Glu His Lys Gly Thr Ile Thr Trp Tyr Lys Asp Asp Ser
385                 390                 395                 400
Lys Thr Pro Val Ser Thr Glu Gln Ala Ser Arg Ile His Gln His Lys
                405                 410                 415
Glu Lys Leu Trp Phe Val Pro Ala Lys Val Glu Asp Ser Gly His Tyr
                420                 425                 430
Tyr Cys Val Val Arg Asn Ser Ser Tyr Cys Leu Arg Ile Lys Ile Ser
                435                 440                 445
Ala Lys Phe Val Glu Asn Glu Pro Asn Leu Cys Tyr Asn Ala Gln Ala
            450                 455                 460
Ile Phe Lys Gln Lys Leu Pro Val Ala Gly Asp Gly Gly Leu Val Cys
465                 470                 475                 480
Pro Tyr Met Glu Phe Phe Lys Asn Glu Asn Asn Glu Leu Pro Lys Leu
                485                 490                 495
Gln Trp Tyr Lys Asp Cys Lys Pro Leu Leu Leu Asp Asn Ile His Phe
                500                 505                 510
Ser Gly Val Lys Asp Arg Leu Ile Val Met Asn Val Ala Glu Lys His
            515                 520                 525
Arg Gly Asn Tyr Thr Cys His Ala Ser Tyr Thr Tyr Leu Gly Lys Gln
            530                 535                 540
Tyr Pro Ile Thr Arg Val Ile Glu Phe Ile Thr Leu Glu Glu Asn Lys
545                 550                 555                 560
Pro Thr Arg Pro Val Ile Val Ser Pro Ala Asn Glu Thr Met Glu Val
                565                 570                 575
Asp Leu Gly Ser Gln Ile Gln Leu Ile Cys Asn Val Thr Gly Gln Leu
                580                 585                 590
Ser Asp Ile Ala Tyr Trp Lys Trp Asn Gly Ser Val Ile Asp Glu Asp
            595                 600                 605
Asp Pro Val Leu Gly Glu Asp Tyr Tyr Ser Val Glu Asn Pro Ala Asn
            610                 615                 620
Lys Arg Arg Ser Thr Leu Ile Thr Val Leu Asn Ile Ser Glu Ile Glu
625                 630                 635                 640
Ser Arg Phe Tyr Lys His Pro Phe Thr Cys Phe Ala Lys Asn Thr His
                645                 650                 655
```

-continued

Gly Ile Asp Ala Ala Tyr Ile Gln Leu Ile Tyr Pro Val Thr Asn Ser
        660                 665                 670

Gly Asp Lys Thr His Thr Cys Pro Cys Pro Ala Pro Glu Leu Leu
        675                 680                 685

Gly Gly Pro Ser Val Phe Leu Phe Pro Pro Lys Pro Lys Asp Thr Leu
        690                 695                 700

Met Ile Ser Arg Thr Pro Glu Val Thr Cys Val Val Val Asp Val Ser
705                 710                 715                 720

His Glu Asp Pro Glu Val Lys Phe Asn Trp Tyr Val Asp Gly Val Glu
                725                 730                 735

Val His Asn Ala Lys Thr Lys Pro Arg Glu Glu Gln Tyr Asn Ser Thr
        740                 745                 750

Tyr Arg Val Val Ser Val Leu Thr Val Leu His Gln Asp Trp Leu Asn
        755                 760                 765

Gly Lys Glu Tyr Lys Cys Lys Val Ser Asn Lys Ala Leu Pro Ala Pro
        770                 775                 780

Ile Glu Lys Thr Ile Ser Lys Ala Lys Gly Gln Pro Arg Glu Pro Gln
785                 790                 795                 800

Val Tyr Thr Leu Pro Pro Ser Arg Asp Glu Leu Thr Lys Asn Gln Val
                805                 810                 815

Ser Leu Thr Cys Leu Val Lys Gly Phe Tyr Pro Ser Asp Ile Ala Val
        820                 825                 830

Glu Trp Glu Ser Asn Gly Gln Pro Glu Asn Asn Tyr Lys Thr Thr Pro
        835                 840                 845

Pro Val Leu Asp Ser Asp Gly Ser Phe Phe Leu Tyr Ser Lys Leu Thr
850                 855                 860

Val Asp Lys Ser Arg Trp Gln Gln Gly Asn Val Phe Ser Cys Ser Val
865                 870                 875                 880

Met His Glu Ala Leu His Asn His Tyr Thr Gln Lys Ser Leu Ser Leu
                885                 890                 895

Ser Pro Gly Lys
        900

<210> SEQ ID NO 11
<211> LENGTH: 2709
<212> TYPE: DNA
<213> ORGANISM: Homo sapiens

<400> SEQUENCE: 11
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta gcaggaccg ggaccttgag      240 gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca agttgcatt ccccttggaa gttgttcaaa aagacagctg tttcaattcc      420
cccatgaaac tcccagtgca taactgtat atagaatatg gcattcagag gatcacttgt     480
ccaaatgtag atggatattt tccttccagt gtcaaaccga ctatcacttg gtatatgggc     540
tgttataaaa tacagaattt taataatgta aatacccgaag gtatgaactt gagtttcctc   600
attgccttaa tttcaaataa tggaaattac acatgtgttg ttacatatcc agaaaatgga     660

```
cgtacgtttc atctcaccag gactctgact gtaaaggtag taggctctcc aaaaaatgca      720 gtgcccctg  tgatccattc acctaatgat catgtggtct atgagaaaga accaggagag      780
gagctactca ttccctgtac ggtctatttt agttttctga tggattctcg caatgaggtt      840
tggtggacca ttgatggaaa aaacctgat  gacatcacta ttgatgtcac cattaacgaa      900
agtataagtc atagtagaac agaagatgaa acaagaactc agattttgag catcaagaaa      960
gttacctctg aggatctcaa gcgcagctat gtctgtcatg ctagaagtgc caaaggcgaa     1020
gttgccaaag cagccaaggt gaagcagaaa gtgccagctc aagatacac  agtggaaaaa     1080 tgcaaggaac gtgaagaaaa aataatttta gtgagctcag caaatgaaat cgatgttcgt     1140
ccctgtcctc ttaacccaaa tgaacacaaa ggcactataa cttggtataa ggatgacagc     1200
aagacacctg tatctacaga acaagcctcc aggattcatc aacacaaaga gaaactttgg     1260
tttgttcctg ctaaggtgga ggattcagga cattactatt gcgtggtaag aaattcatct     1320
tactgcctca gaattaaaat aagtgcaaaa tttgtggaga tgagcctaa  cttatgttat     1380 aatgcacaag ccatatttaa gcagaaacta cccgttgcag gagacggagg acttgtgtgc     1440
ccttatatgg agttttttaa aaatgaaaat aatgagttac ctaaattaca gtggtataag     1500
gattgcaaac ctctacttct tgacaatata cactttagtg gagtcaaaga taggctcatc     1560
gtgatgaatg tggctgaaaa gcatagaggg aactatactt gtcatgcatc ctacacatac     1620
ttgggcaagc aatatcctat taccgggta  atagaattta ttactctaga ggaaaacaaa     1680
cccacaaggc ctgtgattgt gagcccagct aatgagacaa tggaagtaga cttgggatcc     1740
cagatacaat tgatctgtaa tgtcaccggc cagttgagtg acattgctta ctggaagtgg     1800
aatgggtcag taattgatga agatgaccca gtgctagggg aagactatta cagtgtggaa     1860
aatcctgcaa acaaaagaag gagtaccctc atcacagtgc ttaatatatc ggaaattgag     1920
agtgattttt ataaacatcc atttacctgt tttgccaaga atacacatgg tatagatgca     1980
gcatatatcc agttaatata tccagtcact aattccggag agtccaaata cggtccgcca     2040
tgcccatcat gcccagcacc tgagttcctg gggggaccat cagtcttcct gttcccccca     2100
aaacccaagg acactctcat gatctcccgg acccctgagg tcacgtgcgt ggtggtggac     2160
gtgagccagg aagaccccga ggtccagttc aactggtacg tggatggcgt ggaggtgcat     2220
aatgccaaga caaagccgcg ggaggagcag ttcaacagca cgtaccgtgt ggtcagcgtc     2280
ctcaccgtcc tgcaccagga ctggctgaac ggcaaggagt acaagtgcaa ggtctccaac     2340
aaaggcctcc cgtcctccat cgagaaaacc atctccaaag ccaaagggca gccccgagag     2400
ccacaggtgt acaccctgcc cccatcccag gaggagatga ccaagaacca ggtcagcctg     2460
acctgcctgg tcaaaggctt ctaccccagc gacatcgccg tggagtggga gagcaatggg     2520
cagccggaga acaactacaa gaccacgcct cccgtgctgg actccgacgg ctccttcttc     2580
ctctacagca ggctaaccgt ggacaagagc aggtggcagg aggggaatgt cttctcatgc     2640
tccgtgatgc atgaggctct gcacaaccac tacacacaga gagcctctc  cctgtctctg     2700 ggtaaatga                                                              2709
```

<210> SEQ ID NO 12
<211> LENGTH: 902
<212> TYPE: PRT
<213> ORGANISM: Homo sapiens

<400> SEQUENCE: 12

Met Val Leu Leu Trp Cys Val Val Ser Leu Tyr Phe Tyr Gly Ile Leu

-continued

```
          1               5                  10                 15
Gln Ser Asp Ala Ser Glu Arg Cys Asp Asp Trp Gly Leu Asp Thr Met
                20                  25                 30

Arg Gln Ile Gln Val Phe Glu Asp Glu Pro Ala Arg Ile Lys Cys Pro
            35                  40                 45

Leu Phe Glu His Phe Leu Lys Phe Asn Tyr Ser Thr Ala His Ser Ala
        50                  55                 60

Gly Leu Thr Leu Ile Trp Tyr Trp Thr Arg Gln Asp Arg Asp Leu Glu
65                  70                  75                 80

Glu Pro Ile Asn Phe Arg Leu Pro Glu Asn Arg Ile Ser Lys Glu Lys
                85                  90                 95

Asp Val Leu Trp Phe Arg Pro Thr Leu Leu Asn Asp Thr Gly Asn Tyr
            100                 105                110

Thr Cys Met Leu Arg Asn Thr Thr Tyr Cys Ser Lys Val Ala Phe Pro
        115                 120                125

Leu Glu Val Val Gln Lys Asp Ser Cys Phe Asn Ser Pro Met Lys Leu
        130                 135                140

Pro Val His Lys Leu Tyr Ile Glu Tyr Gly Ile Gln Arg Ile Thr Cys
145                 150                 155                160

Pro Asn Val Asp Gly Tyr Phe Pro Ser Val Lys Pro Thr Ile Thr
            165                 170                175

Trp Tyr Met Gly Cys Tyr Lys Ile Gln Asn Phe Asn Asn Val Ile Pro
            180                 185                190

Glu Gly Met Asn Leu Ser Phe Leu Ile Ala Leu Ile Ser Asn Asn Gly
            195                 200                205

Asn Tyr Thr Cys Val Val Thr Tyr Pro Glu Asn Gly Arg Thr Phe His
        210                 215                220

Leu Thr Arg Thr Leu Thr Val Lys Val Val Gly Ser Pro Lys Asn Ala
225                 230                 235                240

Val Pro Pro Val Ile His Ser Pro Asn Asp His Val Val Tyr Glu Lys
                245                 250                255

Glu Pro Gly Glu Glu Leu Leu Ile Pro Cys Thr Val Tyr Phe Ser Phe
            260                 265                270

Leu Met Asp Ser Arg Asn Glu Val Trp Trp Thr Ile Asp Gly Lys Lys
        275                 280                285

Pro Asp Asp Ile Thr Ile Asp Val Thr Ile Asn Glu Ser Ile Ser His
        290                 295                300

Ser Arg Thr Glu Asp Glu Thr Arg Thr Gln Ile Leu Ser Ile Lys Lys
305                 310                 315                320

Val Thr Ser Glu Asp Leu Lys Arg Ser Tyr Val Cys His Ala Arg Ser
                325                 330                335

Ala Lys Gly Glu Val Ala Lys Ala Ala Lys Val Lys Gln Lys Val Pro
            340                 345                350

Ala Pro Arg Tyr Thr Val Glu Lys Cys Lys Glu Arg Glu Glu Lys Ile
            355                 360                365

Ile Leu Val Ser Ser Ala Asn Glu Ile Asp Val Arg Pro Cys Pro Leu
        370                 375                380

Asn Pro Asn Glu His Lys Gly Thr Ile Thr Trp Tyr Lys Asp Asp Ser
385                 390                 395                400

Lys Thr Pro Val Ser Thr Glu Gln Ala Ser Arg Ile His Gln His Lys
                405                 410                415

Glu Lys Leu Trp Phe Val Pro Ala Lys Val Glu Asp Ser Gly His Tyr
            420                 425                430
```

```
              Tyr Cys Val Val Arg Asn Ser Ser Tyr Cys Leu Arg Ile Lys Ile Ser
                      435                 440                 445

Ala Lys Phe Val Glu Asn Glu Pro Asn Leu Cys Tyr Asn Ala Gln Ala
                      450                 455                 460

Ile Phe Lys Gln Lys Leu Pro Val Ala Gly Asp Gly Leu Val Cys
              465                 470                 475                 480

Pro Tyr Met Glu Phe Phe Lys Asn Glu Asn Glu Leu Pro Lys Leu
                              485                 490                 495

Gln Trp Tyr Lys Asp Cys Lys Pro Leu Leu Asp Asn Ile His Phe
                          500                 505                 510

Ser Gly Val Lys Asp Arg Leu Ile Val Met Asn Val Ala Glu Lys His
                          515                 520                 525

Arg Gly Asn Tyr Thr Cys His Ala Ser Tyr Thr Tyr Leu Gly Lys Gln
                          530                 535                 540

Tyr Pro Ile Thr Arg Val Ile Glu Phe Ile Thr Leu Glu Glu Asn Lys
              545                 550                 555                 560

Pro Thr Arg Pro Val Ile Val Ser Pro Ala Asn Glu Thr Met Glu Val
                              565                 570                 575

Asp Leu Gly Ser Gln Ile Gln Leu Ile Cys Asn Val Thr Gly Gln Leu
                          580                 585                 590

Ser Asp Ile Ala Tyr Trp Lys Trp Asn Gly Ser Val Ile Asp Glu Asp
                          595                 600                 605

Asp Pro Val Leu Gly Glu Asp Tyr Tyr Ser Val Glu Asn Pro Ala Asn
                          610                 615                 620

Lys Arg Arg Ser Thr Leu Ile Thr Val Leu Asn Ile Ser Glu Ile Glu
              625                 630                 635                 640

Ser Arg Phe Tyr Lys His Pro Phe Thr Cys Phe Ala Lys Asn Thr His
                              645                 650                 655

Gly Ile Asp Ala Ala Tyr Ile Gln Leu Ile Tyr Pro Val Thr Asn Ser
                          660                 665                 670

Gly Glu Ser Lys Tyr Gly Pro Pro Cys Pro Ser Cys Pro Ala Pro Glu
                          675                 680                 685

Phe Leu Gly Gly Pro Ser Val Phe Leu Phe Pro Pro Lys Pro Lys Asp
                          690                 695                 700

Thr Leu Met Ile Ser Arg Thr Pro Glu Val Thr Cys Val Val Val Asp
              705                 710                 715                 720

Val Ser Gln Glu Asp Pro Glu Val Gln Phe Asn Trp Tyr Val Asp Gly
                              725                 730                 735

Val Glu Val His Asn Ala Lys Thr Lys Pro Arg Glu Glu Gln Phe Asn
                          740                 745                 750

Ser Thr Tyr Arg Val Val Ser Val Leu Thr Val Leu His Gln Asp Trp
                          755                 760                 765

Leu Asn Gly Lys Glu Tyr Lys Cys Lys Val Ser Asn Lys Gly Leu Pro
                          770                 775                 780

Ser Ser Ile Glu Lys Thr Ile Ser Lys Ala Lys Gly Gln Pro Arg Glu
              785                 790                 795                 800

Pro Gln Val Tyr Thr Leu Pro Pro Ser Gln Glu Glu Met Thr Lys Asn
                              805                 810                 815

Gln Val Ser Leu Thr Cys Leu Val Lys Gly Phe Tyr Pro Ser Asp Ile
                          820                 825                 830

Ala Val Glu Trp Glu Ser Asn Gly Gln Pro Glu Asn Asn Tyr Lys Thr
                          835                 840                 845
```

```
Thr Pro Pro Val Leu Asp Ser Asp Gly Ser Phe Phe Leu Tyr Ser Arg
    850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
                885                 890                 895

Ser Leu Ser Leu Gly Lys
            900

<210> SEQ ID NO 13
<211> LENGTH: 2709
<212> TYPE: DNA
<213> ORGANISM: Homo sapiens

<400> SEQUENCE: 13
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta gcaggaccg ggaccttgag      240 gagccaatta acttccgcct ccccgagaac cgcattagta aggagaaaga tgtgctgtgg     300
ttccggccca ctctcctcaa tgacactggc aactatacct gcatgttaag gaacactaca     360
tattgcagca agttgcatt tcccttggaa gttgttcaaa agacagctg tttcaattcc      420 cccatgaaac tcccagtgca taaactgtat atagaatatg gcattcagag gatcacttgt     480
ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttccctgtac ggtctatttt agttttctga tggattctcg caatgaggtt     840
tggtggacca ttgatggaaa aaacctgat gacatcacta ttgatgtcac cattaacgaa      900
agtataagtc atagtagaac agaagatgaa acaagaactc agattttgag catcaagaaa      960
gttacctctg aggatctcaa gcgcagctat gtctgtcatg ctagaagtgc caaaggcgaa    1020
gttgccaaag cagccaaggt gaagcagaaa gtgccagctc aagatacac agtggaaaaa    1080 tgcaaggaac gtgaagaaaa aataatttta gtgagctcag caaatgaaat cgatgttcgt    1140
ccctgtcctc ttaacccaaa tgaacacaaa ggcactataa cttggtataa ggatgacagc    1200
aagacacctg tatctacaga acaagcctcc aggattcatc aacacaaaga gaaactttgg    1260
tttgttcctg ctaaggtgga ggattcagga cattactatt gcgtggtaag aaattcatct    1320
tactgcctca gaattaaaat aagtgcaaaa tttgtggaga tgagcctaa ctatgttat     1380 aatgcacaag ccatatttaa gcagaaacta cccgttgcag agacggagg acttgtgtgc    1440 ccttatatgg agttttttaa aaatgaaaat aatgagttac taaattaca gtggtataag    1500 gattgcaaac ctctacttct tgacaatata cactttagtg gagtcaaaga taggctcatc    1560
gtgatgaatg tggctgaaaa gcatagaggg aactatactt gtcatgcatc ctacacatac    1620
ttgggcaagc aatatcctat tacccgggta atagaattta ttactctaga ggaaaacaaa    1680
cccacaaggc ctgtgattgt gagcccagct aatgagacaa tggaagtaga cttgggatcc    1740
cagatacaat tgatctgtaa tgtcaccggc cagttgagtg acattgctta ctggaagtgg    1800
```

-continued

```
aatgggtcag taattgatga agatgaccca gtgctagggg aagactatta cagtgtggaa      1860
aatcctgcaa acaaaagaag gagtaccctc atcacagtgc ttaatatatc ggaaattgag      1920
agtagatttt ataaacatcc atttacctgt tttgccaaga atacacatgg tatagatgca      1980
gcatatatcc agttaatata tccagtcact aattccggag agtccaaata cggtccgcca      2040
tgcccaccat gcccagcacc tgagttcctg gggggaccat cagtcttcct gttcccccca      2100
aaacccaagg acactctcat gatctcccgg acccctgagg tcacgtgcgt ggtggtggac      2160
gtgagccagg aagaccccga ggtccagttc aactggtacg tggatggcgt ggaggtgcat      2220
aatgccaaga caaagccgcg ggaggagcag ttcaacagca cgtaccgtgt ggtcagcgtc      2280
ctcaccgtcc tgcaccagga ctggctgaac ggcaaggagt acaagtgcaa ggtctccaac      2340
aaaggcctcc cgtcctccat cgagaaaacc atctccaaag ccaaagggca gccccgagag      2400
ccacaggtgt acaccctgcc cccatcccag gaggagatga ccaagaacca ggtcagcctg      2460
acctgcctgg tcaaaggctt ctaccccagc gacatcgccg tggagtggga gagcaatggg      2520
cagccggaga acaactacaa gaccacgcct cccgtgctgg actccgacgg ctccttcttc      2580
ctctacagca ggctaaccgt ggacaagagc aggtggcagg aggggaatgt cttctcatgc      2640
tccgtgatgc atgaggctct gcacaaccac tacacacaga gagcctctc cctgtctctg      2700 ggtaaatga                                                              2709
```

<210> SEQ ID NO 14
<211> LENGTH: 902
<212> TYPE: PRT
<213> ORGANISM: Homo sapiens

<400> SEQUENCE: 14

```
Met Val Leu Leu Trp Cys Val Val Ser Leu Tyr Phe Tyr Gly Ile Leu
  1               5                  10                  15

Gln Ser Asp Ala Ser Glu Arg Cys Asp Asp Trp Gly Leu Asp Thr Met
             20                  25                  30

Arg Gln Ile Gln Val Phe Glu Asp Glu Pro Ala Arg Ile Lys Cys Pro
         35                  40                  45

Leu Phe Glu His Phe Leu Lys Phe Asn Tyr Ser Thr Ala His Ser Ala
     50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205
```

```
Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu Lys Cys Lys Glu Arg Glu Lys Ile
        355                 360                 365

Ile Leu Val Ser Ser Ala Asn Glu Ile Asp Val Arg Pro Cys Pro Leu
370                 375                 380

Asn Pro Asn Glu His Lys Gly Thr Ile Thr Trp Tyr Lys Asp Asp Ser
385                 390                 395                 400

Lys Thr Pro Val Ser Thr Glu Gln Ala Ser Arg Ile His Gln His Lys
                405                 410                 415

Glu Lys Leu Trp Phe Val Pro Ala Lys Val Glu Asp Ser Gly His Tyr
            420                 425                 430

Tyr Cys Val Val Arg Asn Ser Ser Tyr Cys Leu Arg Ile Lys Ile Ser
            435                 440                 445

Ala Lys Phe Val Glu Asn Glu Pro Asn Leu Cys Tyr Asn Ala Gln Ala
450                 455                 460

Ile Phe Lys Gln Lys Leu Pro Val Ala Gly Asp Gly Gly Leu Val Cys
465                 470                 475                 480

Pro Tyr Met Glu Phe Phe Lys Asn Glu Asn Asn Glu Leu Pro Lys Leu
                485                 490                 495

Gln Trp Tyr Lys Asp Cys Lys Pro Leu Leu Leu Asp Asn Ile His Phe
            500                 505                 510

Ser Gly Val Lys Asp Arg Leu Ile Val Met Asn Val Ala Glu Lys His
            515                 520                 525

Arg Gly Asn Tyr Thr Cys His Ala Ser Tyr Thr Tyr Leu Gly Lys Gln
530                 535                 540

Tyr Pro Ile Thr Arg Val Ile Glu Phe Ile Thr Leu Glu Glu Asn Lys
545                 550                 555                 560

Pro Thr Arg Pro Val Ile Val Ser Pro Ala Asn Glu Thr Met Glu Val
                565                 570                 575

Asp Leu Gly Ser Gln Ile Gln Leu Ile Cys Asn Val Thr Gly Gln Leu
            580                 585                 590

Ser Asp Ile Ala Tyr Trp Lys Trp Asn Gly Ser Val Ile Asp Glu Asp
            595                 600                 605

Asp Pro Val Leu Gly Glu Asp Tyr Tyr Ser Val Glu Asn Pro Ala Asn
610                 615                 620
```

```
Lys Arg Arg Ser Thr Leu Ile Thr Val Leu Asn Ile Ser Glu Ile Glu
625                 630                 635                 640

Ser Arg Phe Tyr Lys His Pro Phe Thr Cys Phe Ala Lys Asn Thr His
            645                 650                 655

Gly Ile Asp Ala Ala Tyr Ile Gln Leu Ile Tyr Pro Val Thr Asn Ser
        660                 665                 670

Gly Glu Ser Lys Tyr Gly Pro Pro Cys Pro Cys Pro Ala Pro Glu
    675                 680                 685

Phe Leu Gly Gly Pro Ser Val Phe Leu Phe Pro Pro Lys Pro Lys Asp
690                 695                 700

Thr Leu Met Ile Ser Arg Thr Pro Glu Val Thr Cys Val Val Val Asp
705                 710                 715                 720

Val Ser Gln Glu Asp Pro Glu Val Gln Phe Asn Trp Tyr Val Asp Gly
            725                 730                 735

Val Glu Val His Asn Ala Lys Thr Lys Pro Arg Glu Glu Gln Phe Asn
        740                 745                 750

Ser Thr Tyr Arg Val Val Ser Val Leu Thr Val Leu His Gln Asp Trp
    755                 760                 765

Leu Asn Gly Lys Glu Tyr Lys Cys Lys Val Ser Asn Lys Gly Leu Pro
770                 775                 780

Ser Ser Ile Glu Lys Thr Ile Ser Lys Ala Lys Gly Gln Pro Arg Glu
785                 790                 795                 800

Pro Gln Val Tyr Thr Leu Pro Pro Ser Gln Glu Glu Met Thr Lys Asn
            805                 810                 815

Gln Val Ser Leu Thr Cys Leu Val Lys Gly Phe Tyr Pro Ser Asp Ile
        820                 825                 830

Ala Val Glu Trp Glu Ser Asn Gly Gln Pro Glu Asn Asn Tyr Lys Thr
    835                 840                 845

Thr Pro Pro Val Leu Asp Ser Asp Gly Ser Phe Phe Leu Tyr Ser Arg
850                 855                 860

Leu Thr Val Asp Lys Ser Arg Trp Gln Glu Gly Asn Val Phe Ser Cys
865                 870                 875                 880

Ser Val Met His Glu Ala Leu His Asn His Tyr Thr Gln Lys Ser Leu
            885                 890                 895

Ser Leu Ser Leu Gly Lys
            900

<210> SEQ ID NO 15
<211> LENGTH: 2748
<212> TYPE: DNA
<213> ORGANISM: Homo sapiens

<400> SEQUENCE: 15
atggtgcgct tgtacgtgtt ggtaatggga gtttctgcct tcacccttca gcctgcggca      60
cacacagggg ctgccagaag ctgccggttt cgtggggagc attacaagcg ggagttcagg     120
ctggaagggg agcctgtagc cctgaggtgc ccccaggtgc cctactggtt gtgggcctct     180
gtcagccccc gcatcaacct gacatggcat aaaaatgact ctgctaggac ggtcccagga     240
gaagaagaga cacggatgtg ggcccaggac ggtgctctgt ggcttctgcc agccttgcag     300
gaggactctg gcacctacgt ctgcactact agaaatgctt cttactgtga caaaatgtcc     360
attgagctca gagttttgta gaatacagat gctttcctgc cgttcatctc atacccgcaa     420 atttaacct  tgtcaacctc tggggtatta gtatgccctg acctgagtga attcacccgt     480
gacaaaactg acgtgaagat tcaatggtac aaggattctc ttcttttgga taaagacaat     540
```

-continued

```
gagaaatttc taagtgtgag ggggaccact cacttactcg tacacgatgt ggccctggaa    600
gatgctggct attaccgctg tgtcctgaca tttgcccatg aaggccagca atacaacatc    660
actaggagta ttgagctacg catcaagaaa aaaaagaag agaccattcc tgtgatcatt     720
tccccctca agaccatatc agcttctctg ggtcaagac tgacaatccc atgtaaggtg      780
tttctgggaa ccggcacacc cttaaccacc atgctgtggt ggacggccaa tgacacccac    840
atagagagcg cctacccggg aggccgcgtg accgagggc cacgccagga atattcagaa     900
aataatgaga actacattga agtgccattg atttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctcccga gaaccgcatt    1260
agtaaggaga aagatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg aaaaaaacc tgatgacatc    1860
actattgatg tcaccattaa cgaaagtata agtcatagta aacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagacaaa actcacacat gcccaccgtg cccagcacct   2100
gaactcctgg ggggaccgtc agtcttcctc ttcccccaa aacccaagga caccctcatg    2160
atctcccgga cccctgaggt cacatgcgtg gtggtggacg tgagccacga agaccctgag   2220
gtcaagttca actggtacgt ggacggcgtg gaggtgcata atgccaagac aaagccgcgg   2280
gaggagcagt acaacagcac gtaccgtgtg gtcagcgtcc tcaccgtcct gcaccaggac   2340
tggctgaatg gcaaggagta caagtgcaag gtctccaaca aagccctccc agcccccatc   2400
gagaaaacca tctccaaagc caagggcag ccccgagaac cacaggtgta caccctgccc    2460
ccatcccggg atgagctgac caagaaccag gtcagcctga cctgcctggt caaaggcttc   2520
tatcccagcg acatcgccgt ggagtgggag agcaatgggc agccggagaa caactacaag   2580
accacgcctc ccgtgctgga ctccgacggc tccttcttcc tctatagcaa gctcaccgtg   2640
gacaagagca ggtggcagca ggggaacgtc ttctcatgct ccgtgatgca tgaggctctg   2700
cacaaccact acacgcagaa gagcctctcc ctgtctccgg gtaaatga              2748
```

<210> SEQ ID NO 16
<211> LENGTH: 915
<212> TYPE: PRT

<213> ORGANISM: Homo sapiens

<400> SEQUENCE: 16

```
Met Val Arg Leu Tyr Val Leu Val Met Gly Val Ser Ala Phe Thr Leu
1               5                   10                  15
Gln Pro Ala Ala His Thr Gly Ala Ala Arg Ser Cys Arg Phe Arg Gly
            20                  25                  30
Arg His Tyr Lys Arg Glu Phe Arg Leu Glu Gly Glu Pro Val Ala Leu
        35                  40                  45
Arg Cys Pro Gln Val Pro Tyr Trp Leu Trp Ala Ser Val Ser Pro Arg
    50                  55                  60
Ile Asn Leu Thr Trp His Lys Asn Asp Ser Ala Arg Thr Val Pro Gly
65                  70                  75                  80
Glu Glu Glu Thr Arg Met Trp Ala Gln Asp Gly Ala Leu Trp Leu Leu
                85                  90                  95
Pro Ala Leu Gln Glu Asp Ser Gly Thr Tyr Val Cys Thr Thr Arg Asn
            100                 105                 110
Ala Ser Tyr Cys Asp Lys Met Ser Ile Glu Leu Arg Val Phe Glu Asn
        115                 120                 125
Thr Asp Ala Phe Leu Pro Phe Ile Ser Tyr Pro Gln Ile Leu Thr Leu
    130                 135                 140
Ser Thr Ser Gly Val Leu Val Cys Pro Asp Leu Ser Glu Phe Thr Arg
145                 150                 155                 160
Asp Lys Thr Asp Val Lys Ile Gln Trp Tyr Lys Asp Ser Leu Leu Leu
                165                 170                 175
Asp Lys Asp Asn Glu Lys Phe Leu Ser Val Arg Gly Thr Thr His Leu
            180                 185                 190
Leu Val His Asp Val Ala Leu Glu Asp Ala Gly Tyr Tyr Arg Cys Val
        195                 200                 205
Leu Thr Phe Ala His Glu Gly Gln Gln Tyr Asn Ile Thr Arg Ser Ile
    210                 215                 220
Glu Leu Arg Ile Lys Lys Lys Glu Thr Ile Pro Val Ile
225                 230                 235                 240
Ser Pro Leu Lys Thr Ile Ser Ala Ser Leu Gly Ser Arg Leu Thr Ile
                245                 250                 255
Pro Cys Lys Val Phe Leu Gly Thr Gly Thr Pro Leu Thr Thr Met Leu
            260                 265                 270
Trp Trp Thr Ala Asn Asp Thr His Ile Glu Ser Ala Tyr Pro Gly Gly
        275                 280                 285
Arg Val Thr Glu Gly Pro Arg Gln Glu Tyr Ser Glu Asn Asn Glu Asn
    290                 295                 300
Tyr Ile Glu Val Pro Leu Ile Phe Asp Pro Val Thr Arg Glu Asp Leu
305                 310                 315                 320
His Met Asp Phe Lys Cys Val Val His Asn Thr Leu Ser Phe Gln Thr
                325                 330                 335
Leu Arg Thr Thr Val Lys Glu Ala Ser Ser Thr Phe Ser Glu Arg Cys
            340                 345                 350
Asp Asp Trp Gly Leu Asp Thr Met Arg Gln Ile Gln Val Phe Glu Asp
        355                 360                 365
Glu Pro Ala Arg Ile Lys Cys Pro Leu Phe Glu His Phe Leu Lys Phe
    370                 375                 380
Asn Tyr Ser Thr Ala His Ser Ala Gly Leu Thr Leu Ile Trp Tyr Trp
385                 390                 395                 400
```

-continued

```
Thr Arg Gln Asp Arg Asp Leu Glu Glu Pro Ile Asn Phe Arg Leu Pro
            405                 410                 415
Glu Asn Arg Ile Ser Lys Glu Lys Asp Val Leu Trp Phe Arg Pro Thr
        420                 425                 430
Leu Leu Asn Asp Thr Gly Asn Tyr Thr Cys Met Leu Arg Asn Thr Thr
            435                 440                 445
Tyr Cys Ser Lys Val Ala Phe Pro Leu Glu Val Val Gln Lys Asp Ser
450                 455                 460
Cys Phe Asn Ser Pro Met Lys Leu Pro Val His Lys Leu Tyr Ile Glu
465                 470                 475                 480
Tyr Gly Ile Gln Arg Ile Thr Cys Pro Asn Val Asp Gly Tyr Phe Pro
                485                 490                 495
Ser Ser Val Lys Pro Thr Ile Thr Trp Tyr Met Gly Cys Tyr Lys Ile
            500                 505                 510
Gln Asn Phe Asn Asn Val Ile Pro Glu Gly Met Asn Leu Ser Phe Leu
        515                 520                 525
Ile Ala Leu Ile Ser Asn Asn Gly Asn Tyr Thr Cys Val Val Thr Tyr
    530                 535                 540
Pro Glu Asn Gly Arg Thr Phe His Leu Thr Arg Thr Leu Thr Val Lys
545                 550                 555                 560
Val Val Gly Ser Pro Lys Asn Ala Val Pro Pro Val Ile His Ser Pro
                565                 570                 575
Asn Asp His Val Val Tyr Glu Lys Glu Pro Gly Glu Glu Leu Leu Ile
            580                 585                 590
Pro Cys Thr Val Tyr Phe Ser Phe Leu Met Asp Ser Arg Asn Glu Val
        595                 600                 605
Trp Trp Thr Ile Asp Gly Lys Lys Pro Asp Asp Ile Thr Ile Asp Val
    610                 615                 620
Thr Ile Asn Glu Ser Ile Ser His Ser Arg Thr Glu Asp Glu Thr Arg
625                 630                 635                 640
Thr Gln Ile Leu Ser Ile Lys Lys Val Thr Ser Glu Asp Leu Lys Arg
                645                 650                 655
Ser Tyr Val Cys His Ala Arg Ser Ala Lys Gly Glu Val Ala Lys Ala
            660                 665                 670
Ala Lys Val Lys Gln Lys Val Pro Ala Pro Arg Tyr Thr Val Ser Gly
        675                 680                 685
Asp Lys Thr His Thr Cys Pro Pro Cys Pro Ala Pro Glu Leu Leu Gly
    690                 695                 700
Gly Pro Ser Val Phe Leu Phe Pro Pro Lys Pro Lys Asp Thr Leu Met
705                 710                 715                 720
Ile Ser Arg Thr Pro Glu Val Thr Cys Val Val Val Asp Val Ser His
                725                 730                 735
Glu Asp Pro Glu Val Lys Phe Asn Trp Tyr Val Asp Gly Val Glu Val
            740                 745                 750
His Asn Ala Lys Thr Lys Pro Arg Glu Glu Gln Tyr Asn Ser Thr Tyr
        755                 760                 765
Arg Val Val Ser Val Leu Thr Val Leu His Gln Asp Trp Leu Asn Gly
    770                 775                 780
Lys Glu Tyr Lys Cys Lys Val Ser Asn Lys Ala Leu Pro Ala Pro Ile
785                 790                 795                 800
Glu Lys Thr Ile Ser Lys Ala Lys Gly Gln Pro Arg Glu Pro Gln Val
                805                 810                 815
Tyr Thr Leu Pro Pro Ser Arg Asp Glu Leu Thr Lys Asn Gln Val Ser
```

-continued

```
                820             825             830
Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
        900                 905                 910

Pro Gly Lys
        915
```

<210> SEQ ID NO 17
<211> LENGTH: 2754
<212> TYPE: DNA
<213> ORGANISM: Homo sapiens

<400> SEQUENCE: 17

| | |
|---|---|
| atggtgcgct tgtacgtgtt ggtaatggga gtttctgcct tcacccttca gcctgcggca | 60 |
| cacacagggg ctgccagaag ctgccggttt cgtggaggc attacaagcg ggagttcagg | 120 |
| ctggaagggg agcctgtagc cctgaggtgc ccccaggtgc cctactggtt gtgggcctct | 180 |
| gtcagccccc gcatcaacct gacatggcat aaaaatgact ctgctaggac ggtcccagga | 240 |
| gaagaagaga cacggatgtg ggcccaggac ggtgctctgt ggcttctgcc agccttgcag | 300 |
| gaggactctg gcacctacgt ctgcactact agaaatgctt cttactgtga caaaatgtcc | 360 |
| attgagctca gagtttttga gaatacagat gctttcctgc cgttcatctc atacccgcaa | 420 |
| attttaacct tgtcaacctc tgggtatta gtatgccctg acctgagtga attcacccgt | 480 |
| gacaaaactg acgtgaagat caatggtac aaggattctc ttcttttgga taaagacaat | 540 |
| gagaaatttc taagtgtgag ggggaccact cacttactcg tacacgatgt ggccctggaa | 600 |
| gatgctggct attaccgctg tgtcctgaca tttgcccatg aaggccagca atacaacatc | 660 |
| actaggagta ttgagctacg catcaagaaa aaaaagaag agaccattcc tgtgatcatt | 720 |
| tccccctca agaccatatc agcttctctg gggtcaagac tgacaatccc atgtaaggtg | 780 |
| tttctgggaa ccggcacacc cttaaccacc atgctgtggt ggacggccaa tgacacccac | 840 |
| atagagagcg cctacccggg aggccgcgtg accgaggggc acgccagga atattcagaa | 900 |
| ataatgaga actacattga agtgccattg atttttgatc ctgtcacaag agaggatttg | 960 |
| cacatggatt ttaaatgtgt tgtccataat ccctgagttt tcagacact acgcaccaca | 1020 |
| gtcaaggaag cctcctccac gttctcagaa cgctgcgatg actggggact agacaccatg | 1080 |
| aggcaaatcc aagtgtttga agatgagcca gctcgcatca gtgcccact ctttgaacac | 1140 |
| ttcttgaaat caactacag cacagcccat tcagctggcc ttactctgat ctggtattgg | 1200 |
| actaggcagg accgggacct tgaggagcca attaacttcc gcctccccga gaaccgcatt | 1260 |
| agtaaggaga agatgtgct gtggttccgg cccactctcc tcaatgacac tggcaactat | 1320 |
| acctgcatgt aaggaacac tacatattgc agcaaagttg catttccctt ggaagttgtt | 1380 |
| caaaaagaca gctgtttcaa ttcccccatg aaactcccag tgcataaact gtatatagaa | 1440 |
| tatggcattc agaggatcac ttgtccaaat gtagatggat attttccttc cagtgtcaaa | 1500 |
| ccgactatca cttggtatat gggctgttat aaaatacaga attttaataa tgtaataccc | 1560 |

```
gaaggtatga acttgagttt cctcattgcc ttaatttcaa ataatggaaa ttacacatgt    1620
gttgttacat atccagaaaa tggacgtacg tttcatctca ccaggactct gactgtaaag    1680
gtagtaggct ctccaaaaaa tgcagtgccc cctgtgatcc attcacctaa tgatcatgtg    1740
gtctatgaga aagaaccagg agaggagcta ctcattccct gtacggtcta ttttagtttt    1800
ctgatggatt ctcgcaatga ggtttggtgg accattgatg aaaaaaaacc tgatgacatc    1860
actattgatg tcaccattaa cgaaagtata agtcatagta aacagaaga tgaaacaaga    1920 actcagattt tgagcatcaa gaaagttacc tctgaggatc tcaagcgcag ctatgtctgt    1980
catgctagaa gtgccaaagg cgaagttgcc aaagcagcca aggtgaagca gaaagtgcca    2040
gctccaagat acacagtgtc cggagagtcc aaatacggtc cgccatgccc atcatgccca    2100
gcacctgagt tcctgggggg accatcagtc ttcctgttcc ccccaaaacc caaggacact    2160
ctcatgatct cccggacccc tgaggtcacg tgcgtggtgg tggacgtgag ccaggaagac    2220
cccgaggtcc agttcaactg gtacgtggat ggcgtggagg tgcataatgc caagacaaag    2280
ccgcgggagg agcagttcaa cagcacgtac cgtgtggtca gcgtcctcac cgtcctgcac    2340
caggactggc tgaacggcaa ggagtacaag tgcaaggtct ccaacaaagg cctcccgtcc    2400
tccatcgaga aaaccatctc caaagccaaa gggcagcccc gagagccaca ggtgtacacc    2460
ctgcccccat cccaggagga gatgaccaag aaccaggtca gcctgacctg cctggtcaaa    2520
ggcttctacc ccagcgacat cgccgtggag tgggagagca atgggcagcc ggagaacaac    2580
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754

<210> SEQ ID NO 18
<211> LENGTH: 917
<212> TYPE: PRT
<213> ORGANISM: Homo sapiens

<400> SEQUENCE: 18

Met Val Arg Leu Tyr Val Leu Val Met Gly Val Ser Ala Phe Thr Leu
1               5                   10                  15

Gln Pro Ala Ala His Thr Gly Ala Ala Arg Ser Cys Arg Phe Arg Gly
            20                  25                  30

Arg His Tyr Lys Arg Glu Phe Arg Leu Glu Gly Glu Pro Val Ala Leu
        35                  40                  45

Arg Cys Pro Gln Val Pro Tyr Trp Leu Trp Ala Ser Val Ser Pro Arg
    50                  55                  60

Ile Asn Leu Thr Trp His Lys Asn Asp Ser Ala Arg Thr Val Pro Gly
65                  70                  75                  80

Glu Glu Glu Thr Arg Met Trp Ala Gln Asp Gly Ala Leu Trp Leu Leu
                85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160
```

-continued

```
Asp Lys Thr Asp Val Lys Ile Gln Trp Tyr Lys Asp Ser Leu Leu Leu
                165                 170                 175
Asp Lys Asp Asn Glu Lys Phe Leu Ser Val Arg Gly Thr Thr His Leu
            180                 185                 190
Leu Val His Asp Val Ala Leu Glu Asp Ala Gly Tyr Tyr Arg Cys Val
        195                 200                 205
Leu Thr Phe Ala His Glu Gly Gln Gln Tyr Asn Ile Thr Arg Ser Ile
    210                 215                 220
Glu Leu Arg Ile Lys Lys Lys Glu Glu Thr Ile Pro Val Ile Ile
225                 230                 235                 240
Ser Pro Leu Lys Thr Ile Ser Ala Ser Leu Gly Ser Arg Leu Thr Ile
                245                 250                 255
Pro Cys Lys Val Phe Leu Gly Thr Gly Thr Pro Leu Thr Thr Met Leu
            260                 265                 270
Trp Trp Thr Ala Asn Asp Thr His Ile Glu Ser Ala Tyr Pro Gly Gly
        275                 280                 285
Arg Val Thr Glu Gly Pro Arg Gln Glu Tyr Ser Glu Asn Asn Glu Asn
    290                 295                 300
Tyr Ile Glu Val Pro Leu Ile Phe Asp Pro Val Thr Arg Glu Asp Leu
305                 310                 315                 320
His Met Asp Phe Lys Cys Val Val His Asn Thr Leu Ser Phe Gln Thr
                325                 330                 335
Leu Arg Thr Thr Val Lys Glu Ala Ser Ser Thr Phe Ser Glu Arg Cys
            340                 345                 350
Asp Asp Trp Gly Leu Asp Thr Met Arg Gln Ile Gln Val Phe Glu Asp
        355                 360                 365
Glu Pro Ala Arg Ile Lys Cys Pro Leu Phe Glu His Phe Leu Lys Phe
    370                 375                 380
Asn Tyr Ser Thr Ala His Ser Ala Gly Leu Thr Leu Ile Trp Tyr Trp
385                 390                 395                 400
Thr Arg Gln Asp Arg Asp Leu Glu Glu Pro Ile Asn Phe Arg Leu Pro
                405                 410                 415
Glu Asn Arg Ile Ser Lys Glu Lys Asp Val Leu Trp Phe Arg Pro Thr
            420                 425                 430
Leu Leu Asn Asp Thr Gly Asn Tyr Thr Cys Met Leu Arg Asn Thr Thr
        435                 440                 445
Tyr Cys Ser Lys Val Ala Phe Pro Leu Glu Val Val Gln Lys Asp Ser
    450                 455                 460
Cys Phe Asn Ser Pro Met Lys Leu Pro Val His Lys Leu Tyr Ile Glu
465                 470                 475                 480
Tyr Gly Ile Gln Arg Ile Thr Cys Pro Asn Val Asp Gly Tyr Phe Pro
                485                 490                 495
Ser Ser Val Lys Pro Thr Ile Thr Trp Tyr Met Gly Cys Tyr Lys Ile
            500                 505                 510
Gln Asn Phe Asn Asn Val Ile Pro Glu Gly Met Asn Leu Ser Phe Leu
        515                 520                 525
Ile Ala Leu Ile Ser Asn Asn Gly Asn Tyr Thr Cys Val Val Thr Tyr
    530                 535                 540
Pro Glu Asn Gly Arg Thr Phe His Leu Thr Arg Thr Leu Thr Val Lys
545                 550                 555                 560
Val Val Gly Ser Pro Lys Asn Ala Val Pro Pro Val Ile His Ser Pro
                565                 570                 575
Asn Asp His Val Val Tyr Glu Lys Glu Pro Gly Glu Glu Leu Leu Ile
```

-continued

```
              580             585             590
Pro Cys Thr Val Tyr Phe Ser Phe Leu Met Asp Ser Arg Asn Glu Val
            595                 600                 605
Trp Trp Thr Ile Asp Gly Lys Lys Pro Asp Asp Ile Thr Ile Asp Val
610                 615                 620
Thr Ile Asn Glu Ser Ile Ser His Ser Arg Thr Glu Asp Glu Thr Arg
625                 630                 635                 640
Thr Gln Ile Leu Ser Ile Lys Lys Val Thr Ser Glu Asp Leu Lys Arg
                645                 650                 655
Ser Tyr Val Cys His Ala Arg Ser Ala Lys Gly Glu Val Ala Lys Ala
            660                 665                 670
Ala Lys Val Lys Gln Lys Val Pro Ala Pro Arg Tyr Thr Val Ser Gly
        675                 680                 685
Glu Ser Lys Tyr Gly Pro Pro Cys Pro Ser Cys Pro Ala Pro Glu Phe
    690                 695                 700
Leu Gly Gly Pro Ser Val Phe Leu Phe Pro Pro Lys Pro Lys Asp Thr
705                 710                 715                 720
Leu Met Ile Ser Arg Thr Pro Glu Val Thr Cys Val Val Val Asp Val
                725                 730                 735
Ser Gln Glu Asp Pro Glu Val Gln Phe Asn Trp Tyr Val Asp Gly Val
            740                 745                 750
Glu Val His Asn Ala Lys Thr Lys Pro Arg Glu Glu Gln Phe Asn Ser
        755                 760                 765
Thr Tyr Arg Val Val Ser Val Leu Thr Val Leu His Gln Asp Trp Leu
    770                 775                 780
Asn Gly Lys Glu Tyr Lys Cys Lys Val Ser Asn Lys Gly Leu Pro Ser
785                 790                 795                 800
Ser Ile Glu Lys Thr Ile Ser Lys Ala Lys Gly Gln Pro Arg Glu Pro
                805                 810                 815
Gln Val Tyr Thr Leu Pro Pro Ser Gln Glu Met Thr Lys Asn Gln
            820                 825                 830
Val Ser Leu Thr Cys Leu Val Lys Gly Phe Tyr Pro Ser Asp Ile Ala
        835                 840                 845
Val Glu Trp Glu Ser Asn Gly Gln Pro Glu Asn Asn Tyr Lys Thr Thr
    850                 855                 860
Pro Pro Val Leu Asp Ser Asp Gly Ser Phe Phe Leu Tyr Ser Arg Leu
865                 870                 875                 880
Thr Val Asp Lys Ser Arg Trp Gln Glu Gly Asn Val Phe Ser Cys Ser
                885                 890                 895
Val Met His Glu Ala Leu His Asn His Tyr Thr Gln Lys Ser Leu Ser
            900                 905                 910
Leu Ser Leu Gly Lys
        915

<210> SEQ ID NO 19
<211> LENGTH: 2754
<212> TYPE: DNA
<213> ORGANISM: Homo sapiens

<400> SEQUENCE: 19
atggtgcgct tgtacgtgtt ggtaatggga gtttctgcct tcaccttca gcctgcggca      60 cacacagggg ctgccagaag ctgccggttt cgtgggaggc attacaagcg ggagttcagg    120
ctggaagggg agcctgtagc cctgaggtgc ccccaggtgc cctactggtt gtgggcctct    180
```

```
gtcagccccc gcatcaacct gacatggcat aaaaatgact ctgctaggac ggtcccagga    240
gaagaagaga cacggatgtg ggcccaggac ggtgctctgt ggcttctgcc agccttgcag    300
gaggactctg gcacctacgt ctgcactact agaaatgctt cttactgtga caaaatgtcc    360
attgagctca gagtttttga gaatacagat gctttcctgc cgttcatctc atacccgcaa    420
attttaacct tgtcaacctc tggggtatta gtatgccctg acctgagtga attcacccgt    480
gacaaaactg acgtgaagat tcaatggtac aaggattctc ttcttttgga taaagacaat    540
gagaaatttc taagtgtgag ggggaccact cacttactcg tacacgatgt ggccctggaa    600
gatgctggct attaccgctg tgtcctgaca tttgcccatg aaggccagca atacaacatc    660
actaggagta ttgagctacg catcaagaaa aaaaagaag agaccattcc tgtgatcatt    720
tcccccctca agaccatatc agcttctctg ggtcaagac tgacaatccc atgtaaggtg    780
tttctgggaa ccggcacacc cttaaccacc atgctgtggt ggacggccaa tgacacccac    840
atagagagcg cctacccggg aggccgcgtg accgaggggc cacgccagga atattcagaa    900
aataatgaga actacattga agtgccattg attttttgatc ctgtcacaag agaggatttg    960
cacatggatt ttaaatgtgt tgtccataat accctgagtt ttcagacact acgcaccaca   1020
gtcaaggaag cctcctccac gttctcagaa cgctgcgatg actggggact agacaccatg   1080
aggcaaatcc aagtgtttga agatgagcca gctcgcatca agtgcccact ctttgaacac   1140
ttcttgaaat tcaactacag cacagcccat tcagctggcc ttactctgat ctggtattgg   1200
actaggcagg accgggacct tgaggagcca attaacttcc gcctccccga gaaccgcatt   1260
agtaaggaga agatgtgct gtggttccgg cccactctcc tcaatgacac tggcaactat   1320
acctgcatgt taaggaacac tacatattgc agcaaagttg catttccctt ggaagttgtt   1380
caaaaagaca gctgtttcaa ttcccccatg aaactcccag tgcataaact gtatatagaa   1440
tatggcattc agaggatcac ttgtccaaat gtagatggat attttccttc cagtgtcaaa   1500
ccgactatca cttggtatat gggctgttat aaaatacaga attttaataa tgtaataccc   1560
gaaggtatga acttgagttt cctcattgcc ttaatttcaa ataatggaaa ttacacatgt   1620
gttgttacat atccagaaaa tggacgtacg tttcatctca ccaggactct gactgtaaag   1680
gtagtaggct ctccaaaaaa tgcagtgccc cctgtgatcc attcacctaa tgatcatgtg   1740
gtctatgaga aagaaccagg agaggagcta ctcattccct gtacggtcta ttttagtttt   1800
ctgatggatt ctcgcaatga ggtttggtgg accattgatg gaaaaaaacc tgatgacatc   1860
actattgatg tcaccattaa cgaaagtata agtcatagta gaacagaaga tgaaacaaga   1920
actcagattt tgagcatcaa gaaagttacc tctgaggatc tcaagcgcag ctatgtctgt   1980
catgctagaa gtgccaaagg cgaagttgcc aaagcagcca aggtgaagca gaaagtgcca   2040
gctccaagat acacagtgtc cggagagtcc aaatacggtc cgccatgccc accatgccca   2100
gcacctgagt tcctggggg accatcagtc ttcctgttcc cccaaaaacc caaggacact   2160
ctcatgatct cccggacccc tgaggtcacg tgcgtggtgg tggacgtgag ccaggaagac   2220
cccgaggtcc agttcaactg gtacgtggat ggcgtggagg tgcataatgc caagacaaag   2280
ccgcgggagg agcagttcaa cagcacgtac cgtgtggtca gcgtcctcac cgtcctgcac   2340
caggactggc tgaacggcaa ggagtacaag tgcaaggtct ccaacaaagg cctcccgtcc   2400
tccatcgaga aaaccatctc caaagccaaa gggcagcccc gagagccaca ggtgtacacc   2460
ctgcccccat cccaggagga gatgaccaag aaccaggtca gcctgacctg cctggtcaaa   2520
ggcttctacc ccagcgacat cgccgtggag tgggagagca atgggcagcc ggagaacaac   2580
```

-continued

```
tacaagacca cgcctcccgt gctggactcc gacggctcct tcttcctcta cagcaggcta    2640
accgtggaca agagcaggtg gcaggagggg aatgtcttct catgctccgt gatgcatgag    2700
gctctgcaca accactacac acagaagagc ctctccctgt ctctgggtaa atga          2754
```

<210> SEQ ID NO 20
<211> LENGTH: 917
<212> TYPE: PRT
<213> ORGANISM: Homo sapiens

<400> SEQUENCE: 20

```
Met Val Arg Leu Tyr Val Leu Val Met Gly Val Ser Ala Phe Thr Leu
  1               5                  10                  15

Gln Pro Ala Ala His Thr Gly Ala Ala Arg Ser Cys Arg Phe Arg Gly
             20                  25                  30

Arg His Tyr Lys Arg Glu Phe Arg Leu Glu Gly Glu Pro Val Ala Leu
         35                  40                  45

Arg Cys Pro Gln Val Pro Tyr Trp Leu Trp Ala Ser Val Ser Pro Arg
     50                  55                  60

Ile Asn Leu Thr Trp His Lys Asn Asp Ser Ala Arg Thr Val Pro Gly
 65                  70                  75                  80

Glu Glu Glu Thr Arg Met Trp Ala Gln Asp Gly Ala Leu Trp Leu Leu
                 85                  90                  95

Pro Ala Leu Gln Glu Asp Ser Gly Thr Tyr Val Cys Thr Thr Arg Asn
            100                 105                 110

Ala Ser Tyr Cys Asp Lys Met Ser Ile Glu Leu Arg Val Phe Glu Asn
        115                 120                 125

Thr Asp Ala Phe Leu Pro Phe Ile Ser Tyr Pro Gln Ile Leu Thr Leu
    130                 135                 140

Ser Thr Ser Gly Val Leu Val Cys Pro Asp Leu Ser Glu Phe Thr Arg
145                 150                 155                 160

Asp Lys Thr Asp Val Lys Ile Gln Trp Tyr Lys Asp Ser Leu Leu Leu
                165                 170                 175

Asp Lys Asp Asn Glu Lys Phe Leu Ser Val Arg Gly Thr Thr His Leu
            180                 185                 190

Leu Val His Asp Val Ala Leu Glu Asp Ala Gly Tyr Tyr Arg Cys Val
        195                 200                 205

Leu Thr Phe Ala His Glu Gly Gln Gln Tyr Asn Ile Thr Arg Ser Ile
    210                 215                 220

Glu Leu Arg Ile Lys Lys Lys Lys Glu Glu Thr Ile Pro Val Ile Ile
225                 230                 235                 240

Ser Pro Leu Lys Thr Ile Ser Ala Ser Leu Gly Ser Arg Leu Thr Ile
                245                 250                 255

Pro Cys Lys Val Phe Leu Gly Thr Gly Thr Pro Leu Thr Thr Met Leu
            260                 265                 270

Trp Trp Thr Ala Asn Asp Thr His Ile Glu Ser Ala Tyr Pro Gly Gly
        275                 280                 285

Arg Val Thr Glu Gly Pro Arg Gln Glu Tyr Ser Glu Asn Asn Glu Asn
    290                 295                 300

Tyr Ile Glu Val Pro Leu Ile Phe Asp Pro Val Thr Arg Glu Asp Leu
305                 310                 315                 320

His Met Asp Phe Lys Cys Val Val His Asn Thr Leu Ser Phe Gln Thr
                325                 330                 335

Leu Arg Thr Thr Val Lys Glu Ala Ser Ser Thr Phe Ser Glu Arg Cys
```

-continued

```
                340                 345                 350
Asp Asp Trp Gly Leu Asp Thr Met Arg Gln Ile Gln Val Phe Glu Asp
                355                 360                 365

Glu Pro Ala Arg Ile Lys Cys Pro Leu Phe Glu His Phe Leu Lys Phe
                370                 375                 380

Asn Tyr Ser Thr Ala His Ser Ala Gly Leu Thr Leu Ile Trp Tyr Trp
385                 390                 395                 400

Thr Arg Gln Asp Arg Asp Leu Glu Glu Pro Ile Asn Phe Arg Leu Pro
                    405                 410                 415

Glu Asn Arg Ile Ser Lys Glu Lys Asp Val Leu Trp Phe Arg Pro Thr
                420                 425                 430

Leu Leu Asn Asp Thr Gly Asn Tyr Thr Cys Met Leu Arg Asn Thr Thr
                435                 440                 445

Tyr Cys Ser Lys Val Ala Phe Pro Leu Glu Val Val Gln Lys Asp Ser
                450                 455                 460

Cys Phe Asn Ser Pro Met Lys Leu Pro Val His Lys Leu Tyr Ile Glu
465                 470                 475                 480

Tyr Gly Ile Gln Arg Ile Thr Cys Pro Asn Val Asp Gly Tyr Phe Pro
                    485                 490                 495

Ser Ser Val Lys Pro Thr Ile Thr Trp Tyr Met Gly Cys Tyr Lys Ile
                500                 505                 510

Gln Asn Phe Asn Asn Val Ile Pro Glu Gly Met Asn Leu Ser Phe Leu
                515                 520                 525

Ile Ala Leu Ile Ser Asn Asn Gly Asn Tyr Thr Cys Val Val Thr Tyr
                530                 535                 540

Pro Glu Asn Gly Arg Thr Phe His Leu Thr Arg Thr Leu Thr Val Lys
545                 550                 555                 560

Val Val Gly Ser Pro Lys Asn Ala Val Pro Pro Val Ile His Ser Pro
                    565                 570                 575

Asn Asp His Val Val Tyr Glu Lys Glu Pro Gly Glu Glu Leu Leu Ile
                580                 585                 590

Pro Cys Thr Val Tyr Phe Ser Phe Leu Met Asp Ser Arg Asn Glu Val
                595                 600                 605

Trp Trp Thr Ile Asp Gly Lys Lys Pro Asp Asp Ile Thr Ile Asp Val
610                 615                 620

Thr Ile Asn Glu Ser Ile Ser His Ser Arg Thr Glu Asp Glu Thr Arg
625                 630                 635                 640

Thr Gln Ile Leu Ser Ile Lys Lys Val Thr Ser Glu Asp Leu Lys Arg
                    645                 650                 655

Ser Tyr Val Cys His Ala Arg Ser Ala Lys Gly Glu Val Ala Lys Ala
                660                 665                 670

Ala Lys Val Lys Gln Lys Val Pro Ala Pro Arg Tyr Thr Val Ser Gly
                675                 680                 685

Glu Ser Lys Tyr Gly Pro Pro Cys Pro Pro Cys Pro Ala Pro Glu Phe
                690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
                    725                 730                 735

Ser Gln Glu Asp Pro Glu Val Gln Phe Asn Trp Tyr Val Asp Gly Val
                740                 745                 750

Glu Val His Asn Ala Lys Thr Lys Pro Arg Glu Glu Gln Phe Asn Ser
                755                 760                 765
```

```
Thr Tyr Arg Val Val Ser Val Leu Thr Val Leu His Gln Asp Trp Leu
        770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
                805                 810                 815

Gln Val Tyr Thr Leu Pro Pro Ser Gln Glu Met Thr Lys Asn Gln
                820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
        850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
                885                 890                 895

Val Met His Glu Ala Leu His Asn His Tyr Thr Gln Lys Ser Leu Ser
            900                 905                 910

Leu Ser Leu Gly Lys
        915

<210> SEQ ID NO 21
<211> LENGTH: 2748
<212> TYPE: DNA
<213> ORGANISM: Homo sapiens

<400> SEQUENCE: 21
atggtgcttc tgtggtgtgt agtgagtctc tacttttatg gaatcctgca aagtgatgcc    60
tcagaacgct gcgatgactg gggactagac accatgaggc aaatccaagt gtttgaagat   120
gagccagctc gcatcaagtg cccactcttt gaacacttct tgaaattcaa ctacagcaca   180
gcccattcag ctggccttac tctgatctgg tattggacta ggcaggaccg ggaccttgag   240
gagccaatta cttccgcct ccccgagaac cgcattagta ggagaaaga tgtgctgtgg   300 ttccggccca ctctcctcaa tgacactggc aactatacct gcatgttaag gaacactaca   360
tattgcagca agttgcatt tcccttggaa gttgttcaaa aagacagctg tttcaattcc   420
cccatgaaac tcccagtgca taaactgtat atagaatatg cattcagag atcacttgt    480 ccaaatgtag atgatatttt ccttccagt gtcaaaccga ctatcacttg gtatatgggc   540
tgttataaaa tacagaattt taataatgta atacccgaag gtatgaactt gagtttcctc   600
attgccttaa tttcaaataa tggaaattac acatgtgttg ttacatatcc agaaaatgga   660
cgtacgtttc atctcaccag gactctgact gtaaaggtag taggctctcc aaaaaatgca   720
gtgccccctg tgatccattc acctaatgat catgtggtct atgagaaaga accaggagag   780
gagctactca ttccctgtac ggtctatttt agttttctga tggattctcg caatgaggtt   840
tggtggacca ttgatggaaa aaacctgat gacatcacta ttgatgtcac cattaacgaa   900
agtataagtc atagtagaac agaagatgaa acaagaactc agattttgag catcaagaaa   960
gttacctctg aggatctcaa gcgcagctat gtctgtcatg ctagaagtgc aaaggcgaa   1020 gttgccaaag cagccaaggt gaagcagaaa gtgccagctc aagatacac agtgcacaca   1080 ggggctgcca gaagctgccg gtttcgtggg aggcattaca gcgggagtt caggctggaa   1140 ggggagcctg tagccctgag gtgcccccag gtgccctact ggttgtgggc ctctgtcagc   1200
```

-continued

```
cccgcatca acctgacatg cataaaaat gactctgcta ggacggtccc aggagaagaa    1260
gagacacgga tgtgggccca ggacggtgct ctgtggcttc tgccagcctt gcaggaggac    1320
tctggcacct acgtctgcac tactagaaat gcttcttact gtgacaaaat gtccattgag    1380
ctcagagttt ttgagaatac agatgctttc ctgccgttca tctcatacccc gcaaattta    1440 accttgtcaa cctctggggt attagtatgc cctgacctga gtgaattcac ccgtgacaaa    1500
actgacgtga agattcaatg gtacaaggat tctcttcttt tggataaaga caatgagaaa    1560
tttctaagtg tgaggggac cactcactta ctcgtacacg atgtggccct ggaagatgct    1620
ggctattacc gctgtgtcct gacatttgcc catgaaggcc agcaatacaa catcactagg    1680
agtattgagc tacgcatcaa gaaaaaaaa gaagagacca ttcctgtgat catttccccc    1740
ctcaagacca tatcagcttc tctggggtca agactgacaa tcccatgtaa ggtgtttctg    1800
ggaaccggca caccttaac caccatgctg tggtggacgg ccaatgacac ccacatagag    1860
agcgcctacc cggaggccg cgtgaccgag gggccacgcc aggaatattc agaaaataat    1920
gagaactaca ttgaagtgcc attgattttt gatcctgtca aagagagga tttgcacatg    1980 gattttaaat gtgttgtcca taatacctg agttttcaga cactacgcac cacagtcaag    2040
gaagcctcct ccacgttctc cggagacaaa actcacacat gcccaccgtg cccagcacct    2100
gaactcctgg gggaccgtc agtcttcctc ttcccccccaa acccaagga caccctcatg    2160 atctcccgga cccctgaggt cacatgcgtg gtggtggacg tgagccacga agaccctgag    2220
gtcaagttca actggtacgt ggacggcgtg gaggtgcata atgccaagac aaagccgcgg    2280
gaggagcagt acaacagcac gtaccgtgtg gtcagcgtcc tcaccgtcct gcaccaggac    2340
tggctgaatg gcaaggagta caagtgcaag gtctccaaca aagccctccc agcccccatc    2400
gagaaaacca tctccaaagc caaagggcag ccccgagaac acaggtgta caccctgccc    2460 ccatcccggg atgagctgac caagaaccag gtcagcctga cctgcctggt caaaggcttc    2520
tatcccagcg acatcgccgt ggagtgggag agcaatgggc agccggagaa caactacaag    2580
accacgcctc ccgtgctgga ctccgacggc tccttcttcc tctatagcaa gctcaccgtg    2640
gacaagagca ggtggcagca ggggaacgtc ttctcatgct ccgtgatgca tgaggctctg    2700
cacaaccact acacgcagaa gagcctctcc ctgtctccgg gtaaatga               2748
```

<210> SEQ ID NO 22
<211> LENGTH: 915
<212> TYPE: PRT
<213> ORGANISM: Homo sapiens

<400> SEQUENCE: 22

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
```

```
                100                 105                 110
Thr Cys Met Leu Arg Asn Thr Thr Tyr Cys Ser Lys Val Ala Phe Pro
            115                 120                 125

Leu Glu Val Val Gln Lys Asp Ser Cys Phe Asn Ser Pro Met Lys Leu
            130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
                180                 185                 190

Glu Gly Met Asn Leu Ser Phe Leu Ile Ala Leu Ile Ser Asn Asn Gly
            195                 200                 205

Asn Tyr Thr Cys Val Val Thr Tyr Pro Glu Asn Gly Arg Thr Phe His
            210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
                260                 265                 270

Leu Met Asp Ser Arg Asn Glu Val Trp Trp Thr Ile Asp Gly Lys Lys
            275                 280                 285

Pro Asp Asp Ile Thr Ile Asp Val Thr Ile Asn Glu Ser Ile Ser His
            290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
            355                 360                 365

Arg Gly Arg His Tyr Lys Arg Glu Phe Arg Leu Glu Gly Glu Pro Val
            370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
                420                 425                 430

Leu Leu Pro Ala Leu Gln Glu Asp Ser Gly Thr Tyr Val Cys Thr Thr
            435                 440                 445

Arg Asn Ala Ser Tyr Cys Asp Lys Met Ser Ile Glu Leu Arg Val Phe
            450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
                500                 505                 510

Leu Leu Asp Lys Asp Asn Glu Lys Phe Leu Ser Val Arg Gly Thr Thr
            515                 520                 525
```

```
His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Thr Ile Pro Val
                565                 570                 575

Ile Ile Ser Pro Leu Lys Thr Ile Ser Ala Ser Leu Gly Ser Arg Leu
                580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
        675                 680                 685

Asp Lys Thr His Thr Cys Pro Pro Cys Pro Ala Pro Glu Leu Leu Gly
    690                 695                 700

Gly Pro Ser Val Phe Leu Phe Pro Pro Lys Pro Lys Asp Thr Leu Met
705                 710                 715                 720

Ile Ser Arg Thr Pro Glu Val Thr Cys Val Val Val Asp Val Ser His
                725                 730                 735

Glu Asp Pro Glu Val Lys Phe Asn Trp Tyr Val Asp Gly Val Glu Val
            740                 745                 750

His Asn Ala Lys Thr Lys Pro Arg Glu Glu Gln Tyr Asn Ser Thr Tyr
        755                 760                 765

Arg Val Val Ser Val Leu Thr Val Leu His Gln Asp Trp Leu Asn Gly
    770                 775                 780

Lys Glu Tyr Lys Cys Lys Val Ser Asn Lys Ala Leu Pro Ala Pro Ile
785                 790                 795                 800

Glu Lys Thr Ile Ser Lys Ala Lys Gly Gln Pro Arg Glu Pro Gln Val
                805                 810                 815

Tyr Thr Leu Pro Pro Ser Arg Asp Glu Leu Thr Lys Asn Gln Val Ser
            820                 825                 830

Leu Thr Cys Leu Val Lys Gly Phe Tyr Pro Ser Asp Ile Ala Val Glu
        835                 840                 845

Trp Glu Ser Asn Gly Gln Pro Glu Asn Asn Tyr Lys Thr Thr Pro Pro
    850                 855                 860

Val Leu Asp Ser Asp Gly Ser Phe Phe Leu Tyr Ser Lys Leu Thr Val
865                 870                 875                 880

Asp Lys Ser Arg Trp Gln Gln Gly Asn Val Phe Ser Cys Ser Val Met
                885                 890                 895

His Glu Ala Leu His Asn His Tyr Thr Gln Lys Ser Leu Ser Leu Ser
            900                 905                 910

Pro Gly Lys
        915

<210> SEQ ID NO 23
<211> LENGTH: 2754
```

<212> TYPE: DNA
<213> ORGANISM: Homo sapiens

<400> SEQUENCE: 23

```
atggtgcttc tgtggtgtgt agtgagtctc tacttttatg gaatcctgca aagtgatgcc        60
tcagaacgct gcgatgactg gggactagac accatgaggc aaatccaagt gtttgaagat       120
gagccagctc gcatcaagtg cccactcttt gaacacttct tgaaattcaa ctacagcaca       180
gcccattcag ctggccttac tctgatctgg tattggacta ggcaggaccg ggaccttgag       240
gagccaatta acttccgcct ccccgagaac cgcattagta aggagaaaga tgtgctgtgg       300
ttccggccca ctctcctcaa tgacactggc aactatacct gcatgttaag gaacactaca       360
tattgcagca aagttgcatt tcccttggaa gttgttcaaa aagacagctg tttcaattcc       420
cccatgaaac tcccagtgca taaactgtat atagaatatg cattcagag gatcacttgt        480
ccaaatgtag atggatattt tccttccagt gtcaaaccga ctatcacttg gtatatgggc       540
tgttataaaa tacagaattt taataatgta atacccgaag gtatgaactt gagtttcctc       600
attgccttaa tttcaaataa tggaaattac acatgtgttg ttacatatcc agaaaatgga       660
cgtacgtttc atctcaccag gactctgact gtaaaggtag taggctctcc aaaaaatgca       720
gtgcccctg tgatccattc acctaatgat catgtggtct atgagaaaga accaggagag        780
gagctactca ttccctgtac ggtctatttt agttttctga tggattctcg caatgaggtt       840
tggtggacca ttgatggaaa aaaacctgat gacatcacta ttgatgtcac cattaacgaa       900
agtataagtc atagtagaac agaagatgaa acaagaactc agattttgag catcaagaaa       960
gttacctctg aggatctcaa gcgcagctat gtctgtcatg ctagaagtgc caaaggcgaa      1020
gttgccaaag cagccaaggt gaagcagaaa gtgccagctc aagatacac agtgcacaca       1080
ggggctgcca gaagctgccg gtttcgtggg aggcattaca gcgggagtt caggctggaa       1140
ggggagcctg tagccctgag gtgccccccag gtgccctact ggttgtgggc ctctgtcagc      1200
ccccgcatca acctgacatg gcataaaaat gactctgcta ggacggtccc aggagaagaa      1260
gagacacgga tgtgggccca ggacggtgct ctgtggcttc tgccagcctt gcaggaggac      1320
tctggcacct acgtctgcac tactagaaat gcttcttact gtgacaaaat gtccattgag      1380
ctcagagttt ttgagaatac agatgctttc ctgccgttca tctcataccc gcaaatttta      1440
accttgtcaa cctctggggt attagtatgc cctgacctga gtgaattcac ccgtgacaaa      1500
actgacgtga agattcaatg gtacaaggat tctcttcttt tggataaaga caatgagaaa      1560
tttctaagtg tgagggggac cactcactta ctcgtacacg atgtggccct ggaagatgct      1620
ggctattacc gctgtgtcct gacatttgcc catgaaggcc agcaatacaa catcactagg      1680
agtattgagc tacgcatcaa gaaaaaaaaa gaagagacca ttcctgtgat catttcccc       1740
ctcaagacca tatcagcttc tctggggtca agactgacaa tcccatgtaa ggtgtttctg      1800
ggaaccggca caccccttaac caccatgctg tggtggacgg ccaatgacac ccacatagag      1860
agcgcctacc cggaggccg cgtgaccgag gggccacgcc aggaatattc agaaaataat      1920
gagaactaca ttgaagtgcc attgattttt gatcctgtca agagagga tttgcacatg        1980
gattttaaat gtgttgtcca taatacctg agttttcaga cactacgcac acagtcaag       2040
gaagcctcct ccacgttctc cggagagtcc aaatacggtc cgccatgccc atcatgccca      2100
gcacctgagt tcctgggggg accatcagtc ttcctgttcc ccccaaaacc caaggacact      2160
ctcatgatct cccggacccc tgaggtcacg tgcgtggtgg tggacgtgag ccaggaagac      2220
```

```
cccgaggtcc agttcaactg gtacgtggat ggcgtggagg tgcataatgc caagacaaag    2280
ccgcgggagg agcagttcaa cagcacgtac cgtgtggtca cgtcctcac cgtcctgcac     2340 caggactggc tgaacggcaa ggagtacaag tgcaaggtct ccaacaaagg cctcccgtcc    2400
tccatcgaga aaccatctc caaagccaaa gggcagcccc gagagccaca ggtgtacacc     2460
ctgcccccat cccaggagga gatgaccaag aaccaggtca gcctgacctg cctggtcaaa    2520
ggcttctacc ccagcgacat cgccgtggag tgggagagca tgggcagcc ggagaacaac     2580 tacaagacca cgcctcccgt gctggactcc gacggctcct tcttcctcta cagcaggcta    2640
accgtggaca gagcaggtg gcaggagggg aatgtcttct catgctccgt gatgcatgag     2700
gctctgcaca accactacac acagaagagc ctctccctgt ctctgggtaa atga          2754
```

<210> SEQ ID NO 24
<211> LENGTH: 917
<212> TYPE: PRT
<213> ORGANISM: Homo sapiens

<400> SEQUENCE: 24

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
            20                  25                  30

Arg Gln Ile Gln Val Phe Glu Asp Glu Pro Ala Arg Ile Lys Cys Pro
        35                  40                  45

Leu Phe Glu His Phe Leu Lys Phe Asn Tyr Ser Thr Ala His Ser Ala
    50                  55                  60

Gly Leu Thr Leu Ile Trp Tyr Trp Thr Arg Gln Asp Arg Asp Leu Glu
65                  70                  75                  80

Glu Pro Ile Asn Phe Arg Leu Pro Glu Asn Arg Ile Ser Lys Glu Lys
                85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
    130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285
```

-continued

```
Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Lys Val Lys Gln Lys Val Pro
                340                 345                 350

Ala Pro Arg Tyr Thr Val His Thr Gly Ala Ala Arg Ser Cys Arg Phe
            355                 360                 365

Arg Gly Arg His Tyr Lys Arg Glu Phe Arg Leu Glu Gly Glu Pro Val
    370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
    435                 440                 445

Arg Asn Ala Ser Tyr Cys Asp Lys Met Ser Ile Glu Leu Arg Val Phe
    450                 455                 460

Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
                485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
    515                 520                 525

His Leu Leu Val His Asp Val Ala Leu Glu Asp Ala Gly Tyr Tyr Arg
    530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
                580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
    610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
    675                 680                 685

Glu Ser Lys Tyr Gly Pro Pro Cys Pro Ser Cys Pro Ala Pro Glu Phe
    690                 695                 700
```

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
            725                 730                 735

Ser Gln Glu Asp Pro Glu Val Gln Phe Asn Trp Tyr Val Asp Gly Val
        740                 745                 750

Glu Val His Asn Ala Lys Thr Lys Pro Arg Glu Glu Gln Phe Asn Ser
    755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
            805                 810                 815

Gln Val Tyr Thr Leu Pro Pro Ser Gln Glu Glu Met Thr Lys Asn Gln
        820                 825                 830

Val Ser Leu Thr Cys Leu Val Lys Gly Phe Tyr Pro Ser Asp Ile Ala
    835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880

Thr Val Asp Lys Ser Arg Trp Gln Glu Gly Asn Val Phe Ser Cys Ser
            885                 890                 895

Val Met His Glu Ala Leu His Asn His Tyr Thr Gln Lys Ser Leu Ser
        900                 905                 910

Leu Ser Leu Gly Lys
        915

<210> SEQ ID NO 25
<211> LENGTH: 2754
<212> TYPE: DNA
<213> ORGANISM: Homo sapiens

<400> SEQUENCE: 25
atggtgcttc tgtggtgtgt agtgagtctc tacttttatg gaatcctgca aagtgatgcc      60
tcagaacgct gcgatgactg gggactagac accatgaggc aaatccaagt gtttgaagat     120
gagccagctc gcatcaagtg cccactcttt gaacacttct tgaaattcaa ctacagcaca     180
gcccattcag ctggccttac tctgatctgg tattggacta ggcaggaccg ggaccttgag     240
gagccaatta acttccgcct ccccgagaac cgcattagta aggagaaaga tgtgctgtgg     300
ttccggccca ctctcctcaa tgacactggc aactataccc tgcatgttaa gaacactaca     360
tattgcagca agttgcatt tccccttggaa gttgttcaaa agacagctg tttcaattcc     420 cccatgaaac tcccagtgca taaactgtat atagaatatg cattcagag atcacttgt     480 ccaaatgtag atggatattt tccttccagt gtcaaaccga ctatcacttg gtatatgggc     540
tgttataaaa tacagaattt taataatgta atacccgaag gtatgaactt gagtttcctc     600
attgccttaa tttcaaataa tggaaattac acatgtgttg ttacatatcc agaaaatgga     660
cgtacgtttc atctcaccag gactctgact gtaaaggtag taggctctcc aaaaaatgca     720
gtgccccctg tgatccattc acctaatgat catgtggtct atgagaaaga accaggagag     780
gagctactca ttcctgtac ggtctatttt agttttctga tggattctcg caatgaggtt     840
tggtggacca ttgatggaaa aaaacctgat gacatcacta ttgatgtcac cattaacgaa     900

```
agtataagtc atagtagaac agaagatgaa acaagaactc agattttgag catcaagaaa       960
gttacctctg aggatctcaa gcgcagctat gtctgtcatg ctagaagtgc caaaggcgaa      1020
gttgccaaag cagccaaggt gaagcagaaa gtgccagctc aagatacac agtgcacaca      1080
ggggctgcca gaagctgccg gtttcgtggg aggcattaca agcgggagtt caggctggaa      1140
ggggagcctg tagccctgag gtgccccag gtgccctact ggttgtgggc ctctgtcagc      1200
ccccgcatca acctgacatg gcataaaaat gactctgcta ggacggtccc aggagaagaa      1260
gagacacgga tgtgggccca ggacggtgct ctgtggcttc tgccagcctt gcaggaggac      1320
tctggcacct acgtctgcac tactagaaat gcttcttact gtgacaaaat gtccattgag      1380
ctcagagttt ttgagaatac agatgctttc ctgccgttca tctcataccc gcaaattta      1440
accttgtcaa cctctggggt attagtatgc cctgacctga gtgaattcac ccgtgacaaa      1500
actgacgtga agattcaatg gtacaaggat tctcttctt tggataaaga caatgagaaa      1560
tttctaagtg tgaggggggac cactcactta ctcgtacacg atgtggccct ggaagatgct      1620
ggctattacc gctgtgtcct gacatttgcc catgaaggcc agcaatacaa catcactagg      1680
agtattgagc tacgcatcaa gaaaaaaaaa gaagagacca ttcctgtgat catttccccc      1740
ctcaagacca tatcagcttc tctggggtca agactgacaa tcccatgtaa ggtgtttctg      1800
ggaaccggca cacccttaac caccatgctg tggtggacgg ccaatgacac ccacatagag      1860
agcgcctacc cggaggccg cgtgaccgag gggccacgcc aggaatattc agaaaataat      1920
gagaactaca ttgaagtgcc attgattttt gatcctgtca aagagagga tttgcacatg      1980
gattttaaat gtgttgtcca taatacctg agttttcaga cactacgcac cacagtcaag      2040
gaagcctcct ccacgttctc cggagagtcc aaatacggtc cgccatgccc accatgccca      2100
gcacctgagt tcctgggggg accatcagtc ttcctgttcc ccccaaaacc caaggacact      2160
ctcatgatct cccggacccc tgaggtcacg tgcgtggtgg tggacgtgag ccaggaagac      2220
cccgaggtcc agttcaactg gtacgtggat ggcgtggagg tgcataatgc caagacaaag      2280
ccgcggggag agcagttcaa cagcacgtac cgtgtggtca gcgtcctcac cgtcctgcac      2340
caggactggc tgaacggcaa ggagtacaag tgcaaggtct ccaacaaagg cctcccgtcc      2400
tccatcgaga aaaccatctc caaagccaaa gggcagcccc gagagccaca ggtgtacacc      2460
ctgcccccat cccaggagga gatgaccaag aaccaggtca gcctgacctg cctggtcaaa      2520
ggcttctacc ccagcgacat cgccgtggag tgggagagca atgggcagcc ggagaacaac      2580
tacaagacca cgcctcccgt gctggactcc gacggctcct tcttcctcta cagcaggcta      2640
accgtggaca gagcaggtg gcaggagggg aatgtcttct catgctccgt gatgcatgag      2700
gctctgcaca accactacac acagaagagc ctctccctgt ctctgggtaa atga           2754
```

<210> SEQ ID NO 26
<211> LENGTH: 917
<212> TYPE: PRT
<213> ORGANISM: Homo sapiens

<400> SEQUENCE: 26

```
Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45
```

-continued

```
Leu Phe Glu His Phe Leu Lys Phe Asn Tyr Ser Thr Ala His Ser Ala
 50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val His Thr Gly Ala Ala Arg Ser Cys Arg Phe
        355                 360                 365

Arg Gly Arg His Tyr Lys Arg Glu Phe Arg Leu Glu Gly Glu Pro Val
370                 375                 380

Ala Leu Arg Cys Pro Gln Val Pro Tyr Trp Leu Trp Ala Ser Val Ser
385                 390                 395                 400

Pro Arg Ile Asn Leu Thr Trp His Lys Asn Asp Ser Ala Arg Thr Val
                405                 410                 415

Pro Gly Glu Glu Glu Thr Arg Met Trp Ala Gln Asp Gly Ala Leu Trp
            420                 425                 430

Leu Leu Pro Ala Leu Gln Glu Asp Ser Gly Thr Tyr Val Cys Thr Thr
        435                 440                 445

Arg Asn Ala Ser Tyr Cys Asp Lys Met Ser Ile Glu Leu Arg Val Phe
450                 455                 460
```

-continued

```
Glu Asn Thr Asp Ala Phe Leu Pro Phe Ile Ser Tyr Pro Gln Ile Leu
465                 470                 475                 480

Thr Leu Ser Thr Ser Gly Val Leu Val Cys Pro Asp Leu Ser Glu Phe
            485                 490                 495

Thr Arg Asp Lys Thr Asp Val Lys Ile Gln Trp Tyr Lys Asp Ser Leu
            500                 505                 510

Leu Leu Asp Lys Asp Asn Glu Lys Phe Leu Ser Val Arg Gly Thr Thr
            515                 520                 525

His Leu Leu Val His Asp Val Ala Leu Glu Asp Ala Gly Tyr Tyr Arg
530                 535                 540

Cys Val Leu Thr Phe Ala His Glu Gly Gln Gln Tyr Asn Ile Thr Arg
545                 550                 555                 560

Ser Ile Glu Leu Arg Ile Lys Lys Lys Glu Glu Thr Ile Pro Val
                565                 570                 575

Ile Ile Ser Pro Leu Lys Thr Ile Ser Ala Ser Leu Gly Ser Arg Leu
            580                 585                 590

Thr Ile Pro Cys Lys Val Phe Leu Gly Thr Gly Thr Pro Leu Thr Thr
            595                 600                 605

Met Leu Trp Trp Thr Ala Asn Asp Thr His Ile Glu Ser Ala Tyr Pro
610                 615                 620

Gly Gly Arg Val Thr Glu Gly Pro Arg Gln Glu Tyr Ser Glu Asn Asn
625                 630                 635                 640

Glu Asn Tyr Ile Glu Val Pro Leu Ile Phe Asp Pro Val Thr Arg Glu
                645                 650                 655

Asp Leu His Met Asp Phe Lys Cys Val Val His Asn Thr Leu Ser Phe
            660                 665                 670

Gln Thr Leu Arg Thr Thr Val Lys Glu Ala Ser Ser Thr Phe Ser Gly
            675                 680                 685

Glu Ser Lys Tyr Gly Pro Pro Cys Pro Pro Cys Pro Ala Pro Glu Phe
690                 695                 700

Leu Gly Gly Pro Ser Val Phe Leu Phe Pro Pro Lys Pro Lys Asp Thr
705                 710                 715                 720

Leu Met Ile Ser Arg Thr Pro Glu Val Thr Cys Val Val Val Asp Val
            725                 730                 735

Ser Gln Glu Asp Pro Glu Val Gln Phe Asn Trp Tyr Val Asp Gly Val
            740                 745                 750

Glu Val His Asn Ala Lys Thr Lys Pro Arg Glu Glu Gln Phe Asn Ser
            755                 760                 765

Thr Tyr Arg Val Val Ser Val Leu Thr Val Leu His Gln Asp Trp Leu
770                 775                 780

Asn Gly Lys Glu Tyr Lys Cys Lys Val Ser Asn Lys Gly Leu Pro Ser
785                 790                 795                 800

Ser Ile Glu Lys Thr Ile Ser Lys Ala Lys Gly Gln Pro Arg Glu Pro
            805                 810                 815

Gln Val Tyr Thr Leu Pro Pro Ser Gln Glu Glu Met Thr Lys Asn Gln
            820                 825                 830

Val Ser Leu Thr Cys Leu Val Lys Gly Phe Tyr Pro Ser Asp Ile Ala
            835                 840                 845

Val Glu Trp Glu Ser Asn Gly Gln Pro Glu Asn Asn Tyr Lys Thr Thr
850                 855                 860

Pro Pro Val Leu Asp Ser Asp Gly Ser Phe Phe Leu Tyr Ser Arg Leu
865                 870                 875                 880
```

```
-continued

Thr Val Asp Lys Ser Arg Trp Gln Glu Gly Asn Val Phe Ser Cys Ser
            885                 890                 895

Val Met His Glu Ala Leu His Asn His Tyr Thr Gln Lys Ser Leu Ser
            900                 905                 910

Leu Ser Leu Gly Lys
        915
```